US010786248B2

(12) United States Patent
Rousseau et al.

(10) Patent No.: US 10,786,248 B2
(45) Date of Patent: Sep. 29, 2020

(54) INTRA DERMAL TISSUE FIXATION DEVICE

(71) Applicant: Ethicon, Inc., Somerville, NJ (US)

(72) Inventors: Robert A. Rousseau, Ottsville, PA (US); David C. Lindh, Sr., Flemington, NJ (US)

(73) Assignee: Ethicon. Inc., Somerville, NJ (US)

( * ) Notice: Subject to any disclaimer, the term of this patent is extended or adjusted under 35 U.S.C. 154(b) by 461 days.

(21) Appl. No.: 14/992,128

(22) Filed: Jan. 11, 2016

(65) Prior Publication Data

US 2017/0196554 A1    Jul. 13, 2017

(51) Int. Cl.
| | | |
|---|---|---|
| *A61B 17/068* | (2006.01) | |
| *A61B 17/064* | (2006.01) | |
| *A61B 17/04* | (2006.01) | |
| *A61B 17/08* | (2006.01) | |
| *A61B 17/00* | (2006.01) | |
| *A61B 17/06* | (2006.01) | |
| *A61B 90/00* | (2016.01) | |

(52) U.S. Cl.
CPC ........ *A61B 17/068* (2013.01); *A61B 17/0482* (2013.01); *A61B 17/064* (2013.01); *A61B 17/08* (2013.01); *A61B 2017/00004* (2013.01); *A61B 2017/00349* (2013.01); *A61B 2017/0472* (2013.01); *A61B 2017/06042* (2013.01); *A61B 2017/0647* (2013.01); *A61B 2017/06176* (2013.01); *A61B 2017/081* (2013.01); *A61B 2090/08021* (2016.02)

(58) Field of Classification Search
CPC . A61B 17/0482; A61B 17/064; A61B 17/068; A61B 17/08; A61B 2017/00004; A61B 2017/00349; A61B 2017/0472; A61B 2017/06042; A61B 2017/06176; A61B 2017/0647; A61B 2017/081; A61B 2090/08021
See application file for complete search history.

(56) References Cited

U.S. PATENT DOCUMENTS

| | | | |
|---|---|---|---|
| 3,825,010 | A | 7/1974 | McDonald |
| 4,430,998 | A | 2/1984 | Harvey et al. |
| 4,637,380 | A | 1/1987 | Orejola |

(Continued)

FOREIGN PATENT DOCUMENTS

| | | |
|---|---|---|
| WO | 0121247 A1 | 3/2001 |
| WO | 0145549 A2 | 6/2001 |
| WO | 2009071984 A1 | 6/2009 |

OTHER PUBLICATIONS

International Search Report & Written Opinion dated May 8, 2017 for Application No. USPCT/US17/12732, pp. 22.

*Primary Examiner* — Kathleen S Holwerda
*Assistant Examiner* — Brooke Labranche

(57) ABSTRACT

A device is disclosed for the securement of dermal tissues. The device provides approximation and eversion of the tissue as well as the placement of a fixation element that bridges a wound. The fixation element may be produced in several fixed or dynamic configurations that may or may not alter the ability to engage tissue in response to stresses placed upon the fixation member post-deployment. The delivery device inserts the fastener percutaneously through the epidermis into the sub-dermal position without entering the wound margins with any part of the approximation portion of the delivery device.

9 Claims, 26 Drawing Sheets

(56) References Cited

U.S. PATENT DOCUMENTS

| | | |
|---|---|---|
| 5,047,047 A | 9/1991 | Yoon |
| 5,234,462 A | 8/1993 | Pavletic |
| 5,292,326 A | 3/1994 | Green et al. |
| 5,342,376 A | 8/1994 | Ruff |
| 5,389,102 A | 2/1995 | Green et al. |
| 5,423,856 A | 6/1995 | Green |
| 5,489,287 A | 2/1996 | Green et al. |
| 5,573,541 A | 11/1996 | Green et al. |
| 5,984,949 A | 11/1999 | Levin |
| 6,106,556 A | 8/2000 | Demopulos et al. |
| 6,176,868 B1 | 1/2001 | Detour |
| 6,692,499 B2 | 2/2004 | Törmälä et al. |
| 6,726,705 B2 | 4/2004 | Peterson et al. |
| 7,112,214 B2 | 9/2006 | Peterson et al. |
| 7,686,829 B2 | 3/2010 | Elliott et al. |
| 8,066,737 B2 | 11/2011 | Meade et al. |
| 8,074,857 B2 | 12/2011 | Peterson et al. |
| 8,506,591 B2 | 8/2013 | Danielson et al. |
| 8,632,454 B2 | 1/2014 | Lashinski et al. |
| 9,861,379 B2 | 1/2018 | Chin et al. |
| 2003/0149447 A1 | 8/2003 | Morency et al. |
| 2005/0119694 A1 | 6/2005 | Jacobs et al. |
| 2007/0049969 A1 | 3/2007 | Peterson |
| 2007/0203506 A1 | 8/2007 | Sibbitt, Jr. et al. |
| 2007/0257395 A1 | 11/2007 | Lindh et al. |
| 2008/0300624 A1* | 12/2008 | Schwemberger .... A61B 17/064 606/213 |
| 2008/0319455 A1* | 12/2008 | Harris ................ A61B 17/0684 606/139 |
| 2009/0093824 A1 | 4/2009 | Hasan et al. |
| 2010/0187285 A1 | 7/2010 | Harris et al. |
| 2010/0298871 A1 | 11/2010 | Ruff et al. |
| 2011/0054522 A1 | 3/2011 | Lindh, Sr. et al. |
| 2012/0053603 A1 | 3/2012 | Williamson, IV |
| 2013/0079815 A1 | 3/2013 | Hasan et al. |
| 2013/0267997 A1 | 10/2013 | Peterson et al. |
| 2014/0114390 A1 | 4/2014 | Tobis et al. |
| 2014/0148828 A1* | 5/2014 | Ewers .............. A61B 17/00234 606/153 |
| 2014/0367447 A1 | 12/2014 | Woodard et al. |
| 2015/0173746 A1* | 6/2015 | Baxter, III ....... A61B 17/07207 227/180.1 |
| 2015/0201927 A1* | 7/2015 | Hasan ................ A61B 17/0469 606/145 |

* cited by examiner

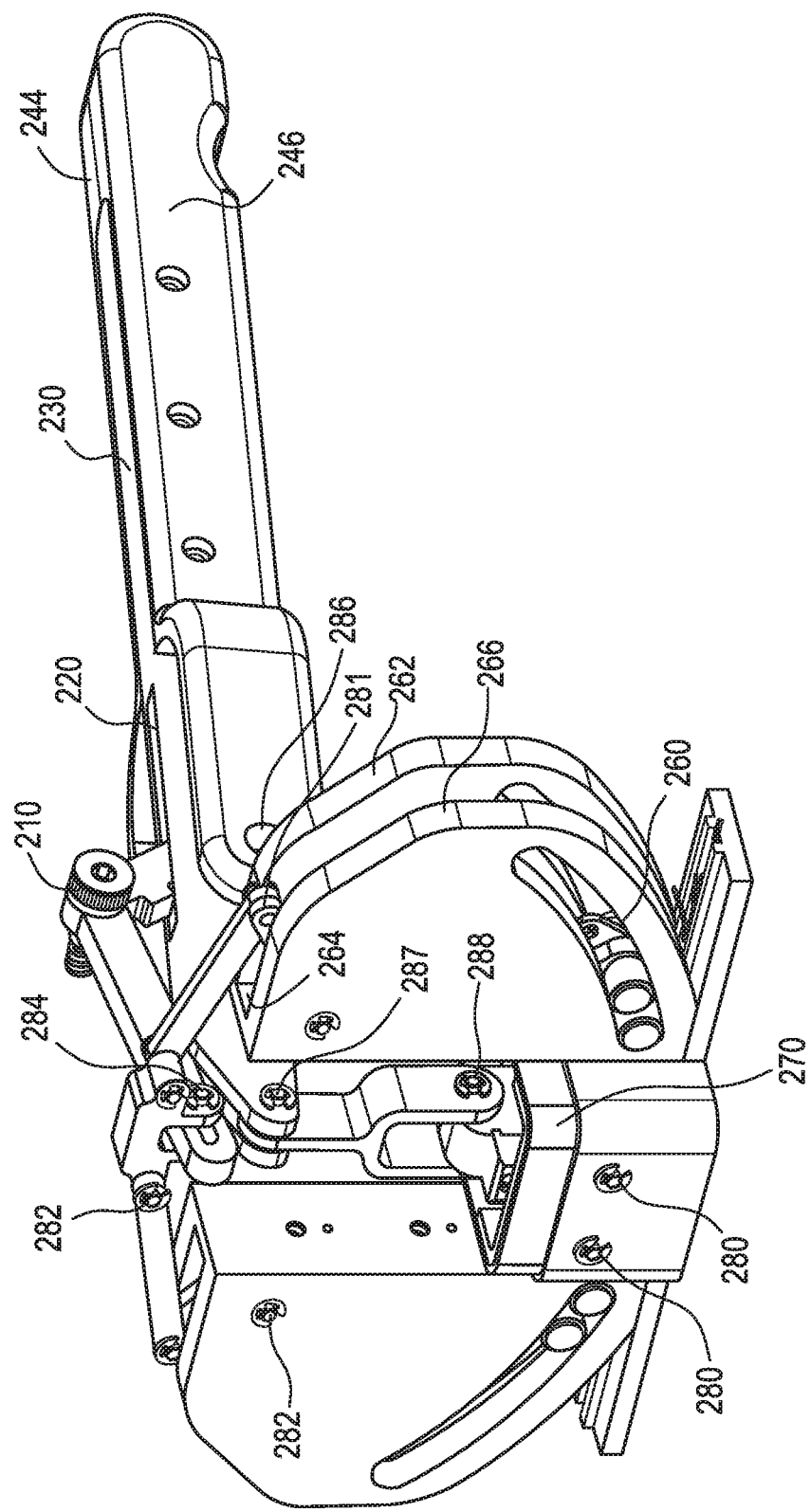

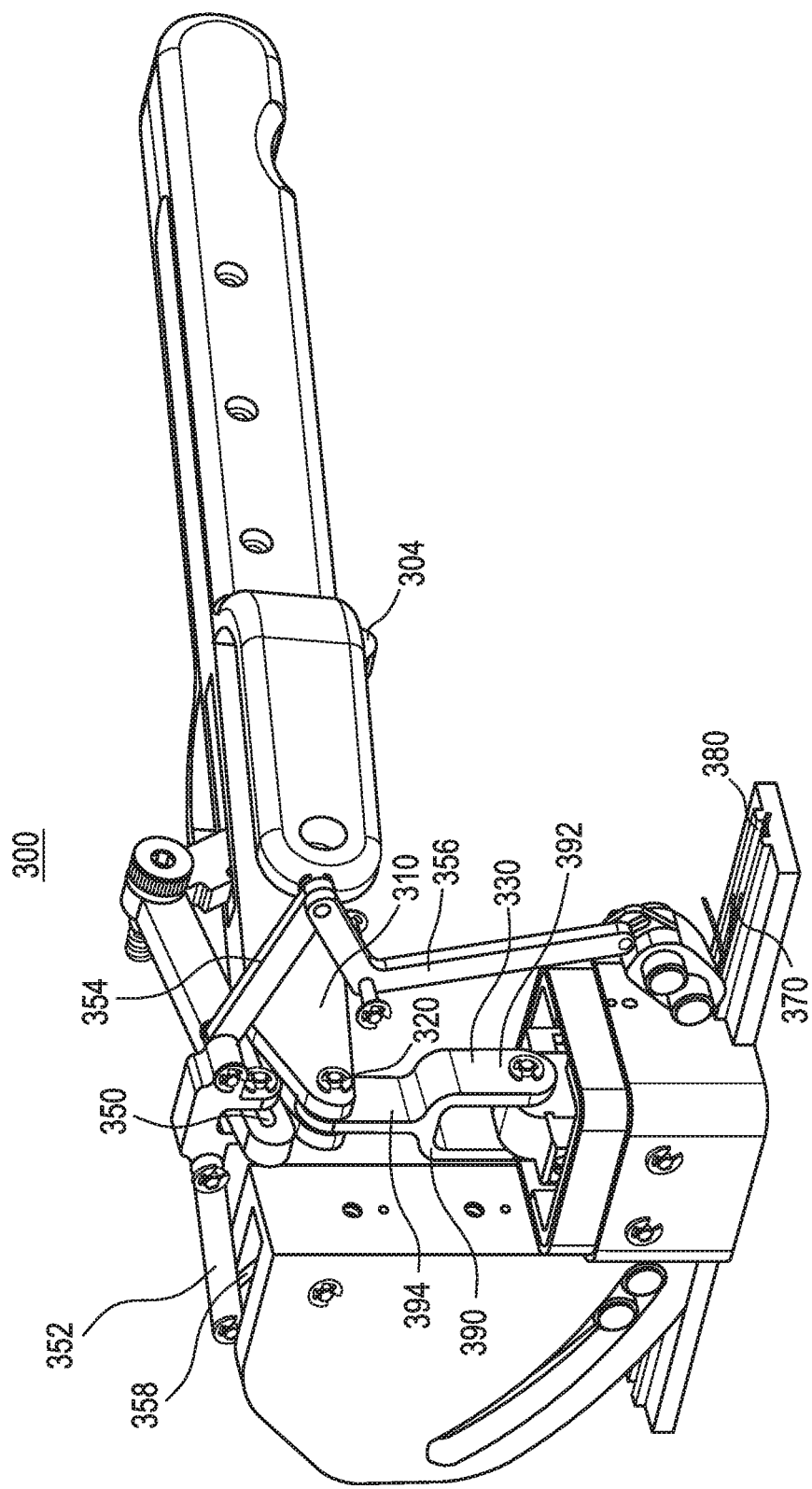

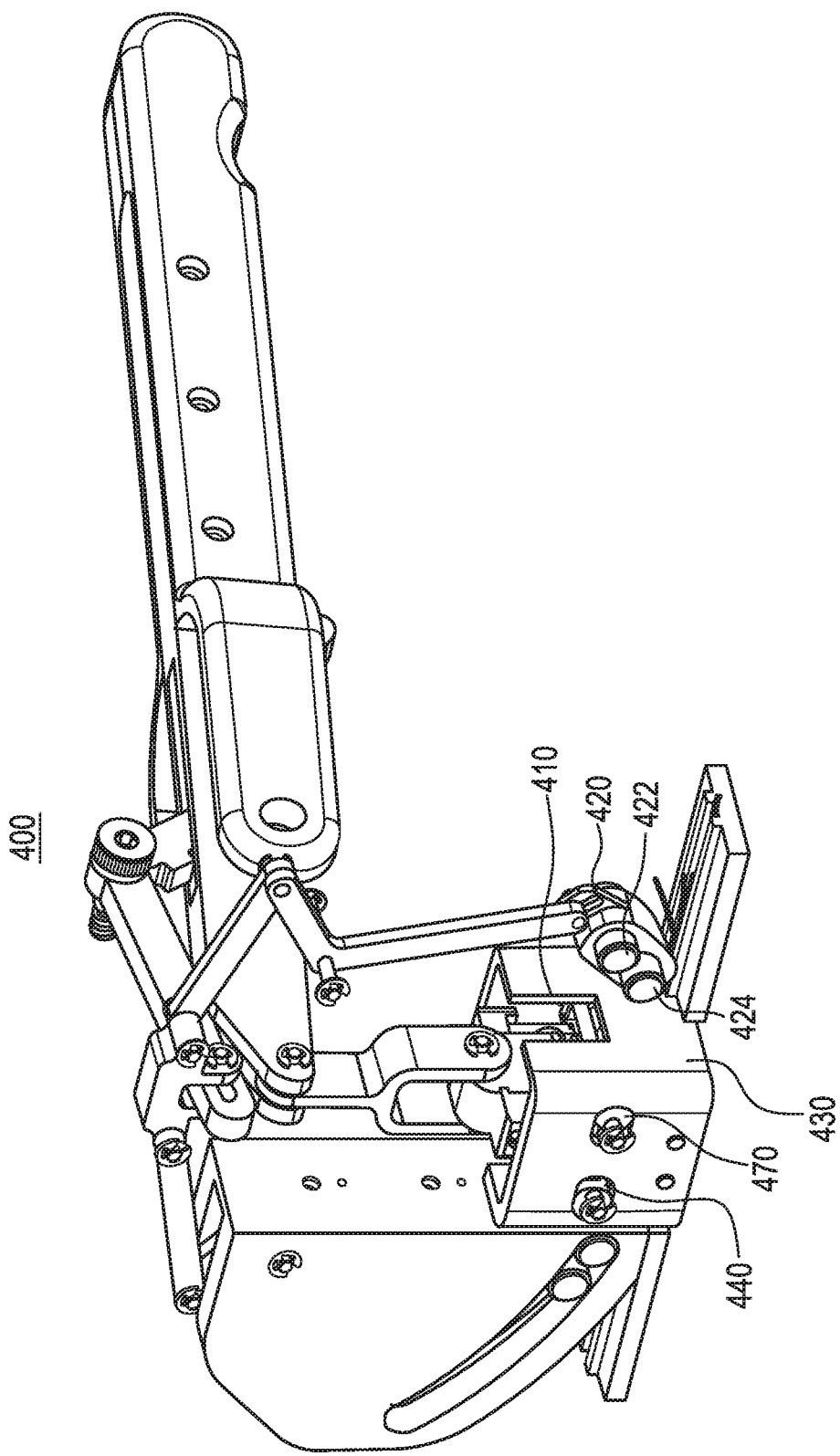

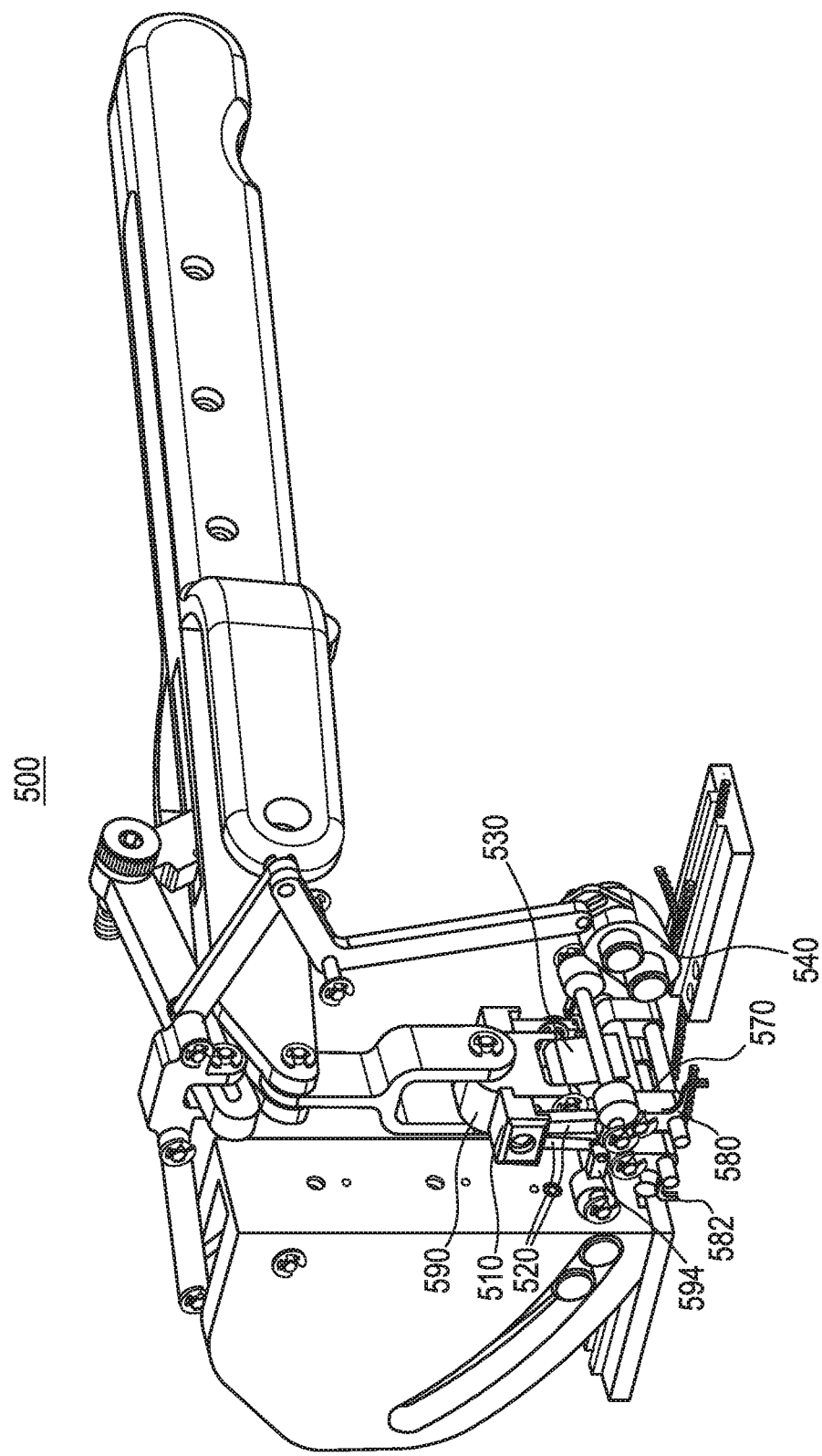

1100

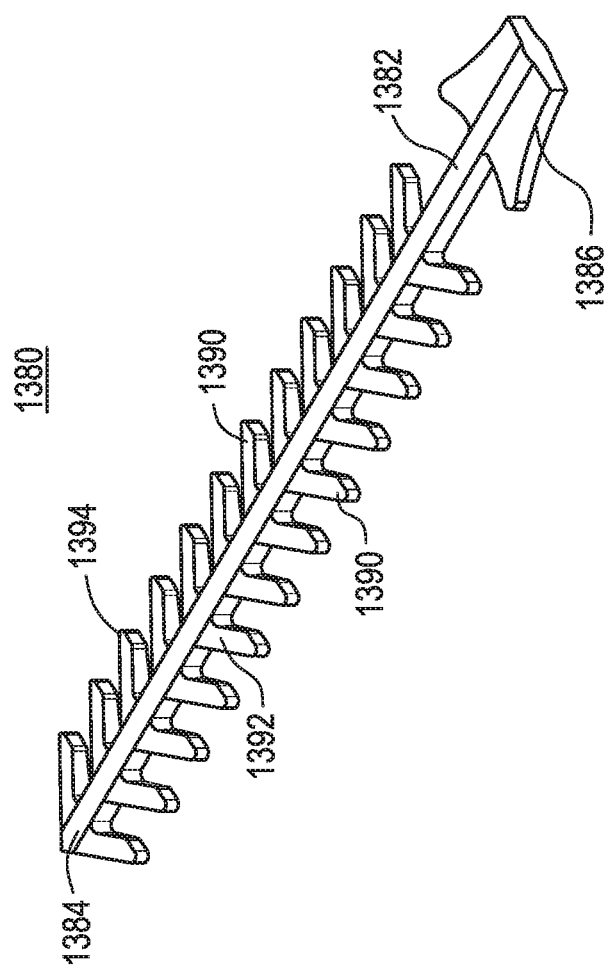

2000

INTRA DERMAL TISSUE FIXATION DEVICE

FIELD OF THE INVENTION

The field of art to which this invention pertains is medical devices for tissue fixation, more particularly devices for applying tissue fixation implants.

BACKGROUND OF THE INVENTION

Biological healing of a tissue opening such as a wound commences through the proximity of the opposed wounded surfaces of living tissue. If the opening is very large or if its location subjects the wound to continual movement, forcibly holding the sides of the opening in close proximity will promote the healing process.

Human skin tissue is comprised of three distinct layers of tissue. The epidermal layer, also known as the epidermis, is the outermost layer and includes non-living tissue cells. The dermal layer, or dermis, is the middle layer directly below the epidermal layer and comprises the living tissue of the skin that is the strongest of the three layers. The subcutaneous, or hypodermis layer is the bottom layer of skin tissue and includes less connective tissue making this the weakest layer of skin tissue.

Healing occurs best when the opposing dermal layers of the skin tissue are held in proximity with each other. The epidermis, or the superficial-most layer of the skin, must be well aligned during wound closure to seal off the wound to prevent the possible invasion of the wound by infectious agents. In order to most effectively close an incision with minimal scarring, it is advantageous to position the opposed first and second sections of skin so as to both be within the same plane (vertical alignment), and to approximate the skin edges as close together as possible (horizontal alignment). If these sections of skin are not well approximated with regard to horizontal alignment, the resulting scar will be relatively wide as the body will fill in the gap with additional connective tissue forming a scar. If the wound edges are not well aligned in the vertical dimension, then the scar will heal with a "step-off" which causes the scar to be more prominent.

While it is important to maintain the edges of the epidermis in close alignment and approximation, the closure of the epidermis alone will not provide sufficient strength or support to the deep dermal layers while the wound is healing.

The dermis is the deeper layer of the skin and is particularly important with regard to proper wound approximation. The dermis is the strongest layer of the skin and wound closure techniques that incorporate the dermis into the closure provide the most structural integrity. Further, it has been demonstrated that wound healing occurs optimally if the approximation of the edges of the dermal wounds maintain the apposed tissues in a slightly protrusive condition at the superficial surface, a desirable wound configuration that is clinically known as "eversion." As the wound heals, the eversion gradually settles, resulting in a flat/optimal scar.

Manual suturing is perhaps the oldest of the available options for effecting a dermal closure. The physician directs a surgical needle, to which is temporarily attached a surgical suturing filament, through one section of skin, across the incision and into the other side of the incision. This process is repeated as many times as necessary to result in a certain number of "stitches" closing the incision. Upon reaching the end of the incision, the physician ties off the last suture to complete the process.

Relatively large incisions in excess of many centimeters may be made in the course of a surgical procedure which can often take the surgeon a very long time to close with sutures. It is not uncommon for the suturing of the incision to take longer than the actual surgical procedure or operation itself. This is also true for large wounds resulting from trauma. Not only is it time consuming, but surgeons often view the process as tedious. Moreover, the repeated movement of the needle through the skin of the patient necessarily increases the risk to the surgeon or assistant of being exposed to a needle prick which in turn can lead to certain transmissions of infectious diseases including, but not limited to, Hepatitis C and HIV.

While traditional suturing remains a popular method of effectuating closure of wound openings, the use of surgical staples and surgical staplers as a closure technique has become increasingly popular, especially in surgical settings where the opening is created through a purposeful incision. In these settings, the incision tends to make a clean, straight cut with the opposing sides of the incision having consistent and non-jagged surfaces. The use of skin stapling offers a means of producing a well-everted and approximated wound edge quickly, thereby overcoming the time element of suturing and the attendant disadvantages and complications.

Generally, in skin stapling, the back span of a metal staple is driven over an anvil causing the metal staple to deform while pressed against the surface of the epidermis. The staple legs penetrate the dermal layers and are folded inward so as to retain the skin tissue in a compressed manner within the staple. This process can be repeated along the length of the wound opening such that the entire incision or wound is held closed during the healing process.

Foremost among the drawbacks associated with surgical skin stapling is the significant scarring associated with the presence of the staples during healing. The scarring is often referred to as "railroad tracks", as the scar will typically include the linear incision itself laterally flanked by pairs of matching demarcations where the prongs of the staple were located. The presence of the transdermal portions of the staples, the leg elements, during healing, will produce a delayed region of healing that subsequently fills in with scar tissue. If the staples are left in place too long there is the potential for the formation of sinus tracks around the transdermal elements. Moreover, staples are significantly more painful to the patient in that they need to be removed after being installed and after the incision is healed.

There remains a need in this field to provide a means for securing the dermal layer in sound approximation, with an everted edge. The method of closure should offer the speed of application associated with skin stapling, while eliminating the transdermal element during healing in order to prevent or minimize scarring.

There have been attempts in the past to try to eliminate some of the disadvantages associated with surgical skin stapling. In U.S. Pat. Nos. 5,292,326; 5,389,102; 5,423,856; 5,489,287; and 5,573,541 Green et al. disclose a dermal stapler that interdigitated the wound edges in an undulating/serpentine configuration. This device then fired straight resorbable pins across the wound edge interdigitations in order to secure the edges of the wound together. This product (referred to as the AutoSuture SQS 20) was believed to be not successful for various reasons, including wound-healing problems which resulted from the undulating/interdigitating wound edge configuration.

In U.S. Pat. Nos. 6,726,705; 7,1112,214; 8,074,857 and US 2013/0267997, Peterson et al. disclose an absorbable dermal stapler wherein the staples are manufactured from a material or anchor which can be absorbed by the patient. The absorbable dermal stapler is marketed under the trademark "Insorb™". The absorbable dermal stapling technology is believed to provide less than optimal horizontal and vertical alignment. The staple that is utilized is a "U" shaped unit with barbed tips. The stapler head is inserted into the wound, between the two opposed wound surfaces to be apposed. The tissue is gathered or pressed against the head of the stapling unit to create two co-planar target zones intended to receive the tips of the staple during deployment. Intrinsically, this method of apposition requires the use of gathering features to attempt to overcome the wedging or separating effect induced by the presence of the stapler head within the region to be joined. The presence of the stapling head within the wound may also present an additional interference at the end of the partially approximated wound. Additionally, the method in which the fasteners hold the wound edges in eversion may result in prominent "dimpling" or "mounding" of the skin where the fasteners secure the skin edges, a closure appearance which can cause concern to surgeons when they use dermal staplers for wound closure.

US 2009/0093824, Hasan et al. discloses a wound closure device which is adapted to position an anchor specifically known as an "H-Type" fastener between first and second sections of skin to be secured. The device includes channels in which the first and second sections of skin are to be positioned and includes a single arcuate shaped rotating needle adapted to enter one section of skin through the sub-dermal layer and carry the H-shaped anchor therewith. While the '824 application attempts to position the first and second sections of skin relative to one another, the use of such an H-shaped anchor does not adequately pull the two sections close together after insertion and thus would result in longer healing times and more scarring than is acceptable. More specifically, the leading prong of the "H" needs to be pulled entirely through the second section of skin in order to deploy. Once it is so deployed and released, the anchor is pulled back by the opposite prong and the normal tension on the wound edges, thus resulting in slack in the anchor and a loose "seam". Moreover, the '824 application uses a system of rotating approximation arms to push the first and second sections of skin toward one another prior to insertion of the anchor from the underside position of the wound. This action of the tissue engagement pulls the tissue edges together, however, as the hook like elements are rotating about an axis located below the tissues to be approximated, it is likely to cause in inversion of the epidermal layer as opposed to the desired eversion. Additionally, intrinsically, this method of apposition requires the use of gathering features to attempt to overcome the wedging or separating effect induced by the presence of the stapler head within the region to be joined. Further, the presence of the deployment head within the wound may also present an additional interference at the end of the partially approximated wound.

In US 2015/0201927, Hasan et al, disclose a device that is able to place suture-like elements in a helical deployment within the dermal layer from within the wound. The device is produced with two counter rotating arcuate needles in two parallel planes of rotation. The suture-like element is produced with needle guide elements located at each end of the suture-like element. The suture-like element and arcuate needles are placed within the margins of the wound and the arcuate needles are rotated through the dermal layer from the subdermal position with the suture-like element located in a somewhat transverse plane. Since the two arcuate needles are rotating about two separate planes, the suture-like element, once deployed through the tissue, is pulled into two distinct planes of rotation, thereby emulating a helical deployment of suture achieved through the traditional single needle pull through method. A deficit of this method of apposition is similar to the limitations of the '857 and '824 devices, this method of apposition also requires the use of gathering features to attempt to overcome the wedging or separating effect induced by the presence of the stapler head within the region to be joined. Further, the presence of the deployment head within the wound may also present an additional interference at the end of the partially approximated wound.

US 2007/0203506, Sibitt et al, disclose a vascular closure device. The device is deployable through a catheter and engages the tissue surrounding the site of the puncture through the use of gripper tines that are able to evert the edges of the tissue in preparation for the application of the cincture or noose component. The device is reliant upon the catheter to provide compression of the tissue as well as counter traction to the surrounding tissue to form a purse-like gathering of tissue. This device would not have utility for general closure of linear incisions as the final approximation of the tissue is similar to the application of a ligation loop to internal tissues. Appropriate tensioning and continued engagement of the tissue in the presence of the inflammatory response of ordinary tissue healing may cause necrosis and subsequent dehiscence.

In US 2007/0049969 Peterson et al. discloses an applicator apparatus that rotatably places non-flexible arcuate fasteners across tissue edges for approximation. The falcate tissue penetrator "carries" a fastener and pushes the fastener through the tissue to approximate and secure the edges. The cross sectional shape of their falcate tissue penetrator is a right angle to the shaft of the delivery device. The unit applies a single fastener during the course of rotation and there is no means for counter-traction to be applied to the tissue in order to keep the tissue engaged with the penetrator during application. As such, the tissue can move away from the penetrator during rotation and result in misaligned tissue edges. Additionally, the device is intended to be utilized within the margins of the wound and thus would suffer from the same wedging effect as detailed for the other devices offering an inter-wound deployment device.

Therefore, there is a need in this art for novel fixation devices for incisions and wounds that implant fasteners in a rapid and simple manner to provide excellent alignment of opposed sides of the dermis along with excellent eversion to provide for superior surgical and patient outcomes. There is also a need for novel methods of closing incisions and wounds to provide for superior outcomes.

SUMMARY OF THE INVENTION

Accordingly, novel tissue fixation devices are disclosed. The tissue fixation devices have a handle member having a proximal end and a distal end, and a top and a bottom. A tissue engagement trigger member having a proximal end and a distal end is pivotally mounted to the distal end of the handle member. A firing trigger is also pivotally mounted to the handle member. A tissue engagement end effector is mounted to the distal end of the handle member and operably coupled to the tissue engagement trigger for engaging and everting tissue. And, an implant placement end effector is mounted to the distal end of the handle member and operably coupled with the firing trigger for delivering a tissue fastener into tissue.

Another aspect of the present invention is a method of approximating a wound using the above described tissue fixation device to approximate and evert tissue and implant a tissue fastener to repair or close a wound or incision in dermal tissue.

Yet another aspect of the present invention is a tissue fastener. The tissue fastener has an elongated central member having a proximal end and a distal end and opposed lateral sides. A plurality of frictional engagement elements extend outwardly from each lateral side such that the engagement members on a first lateral side are opposed to the engagement members extending outwardly from the other lateral side. Each engagement member has a proximal end and a distal end and a cross-sectional area. Each engagement member additionally has a distal tip extending from the distal end, wherein the tip has a cross-sectional area that is smaller than the cross-sectional area of the engagement member.

Still yet another aspect of the present invention is a tissue fastener. The tissue fastener has an elongated central member having a proximal end, a distal end, a top surface, a bottom surface, and opposed lateral sides. A first web member extends from the top surface. The first web member has a bottom and a top, and a plurality of partial circular openings extending through the first web member adjacent to the top surface and intersecting the top surface, wherein the first web member is tapered from the bottom to the top. And, a second web member extends from the bottom surface. The second web member has a bottom and a top, a longitudinal axis, and a plurality of slits at acute angles relative to the longitudinal axis of the second web member, wherein the second web member is tapered from the bottom to the top.

These and other aspects and advantages of the present invention will become more apparent from the following description and accompanying drawings.

BRIEF DESCRIPTION OF THE DRAWINGS

FIG. 2 is a perspective view of the instrument of FIG. 1A that has been partially disassembled.

FIG. 3 is a perspective view of the instrument of FIG. 2 that has been partially disassembled by removing of the opposing wall support structures.

FIG. 4 is a perspective view of the instrument of FIG. 3 with the axle housing removed.

FIG. 5 is a perspective view of the instrument of FIG. 4 showing the linkage elements.

FIG. 13A illustrates an orthogonal view of a directional fastener useful with the novel tissue fixation instruments of the present invention.

DETAILED DESCRIPTION OF THE INVENTION

Figure 1A:
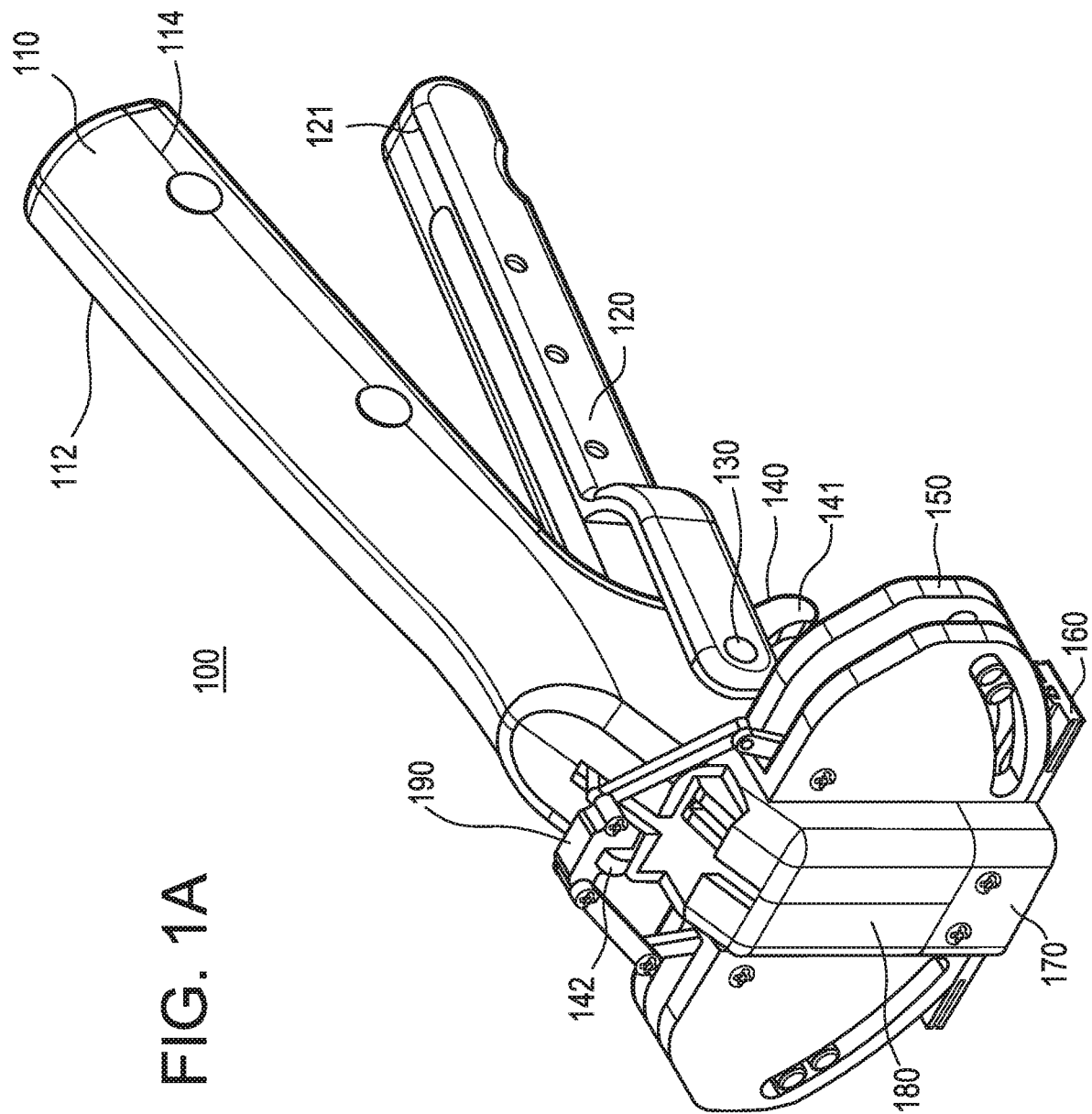
FIG. 1A is a perspective view of a tissue fixation instrument of the present invention.
Figure 1B:
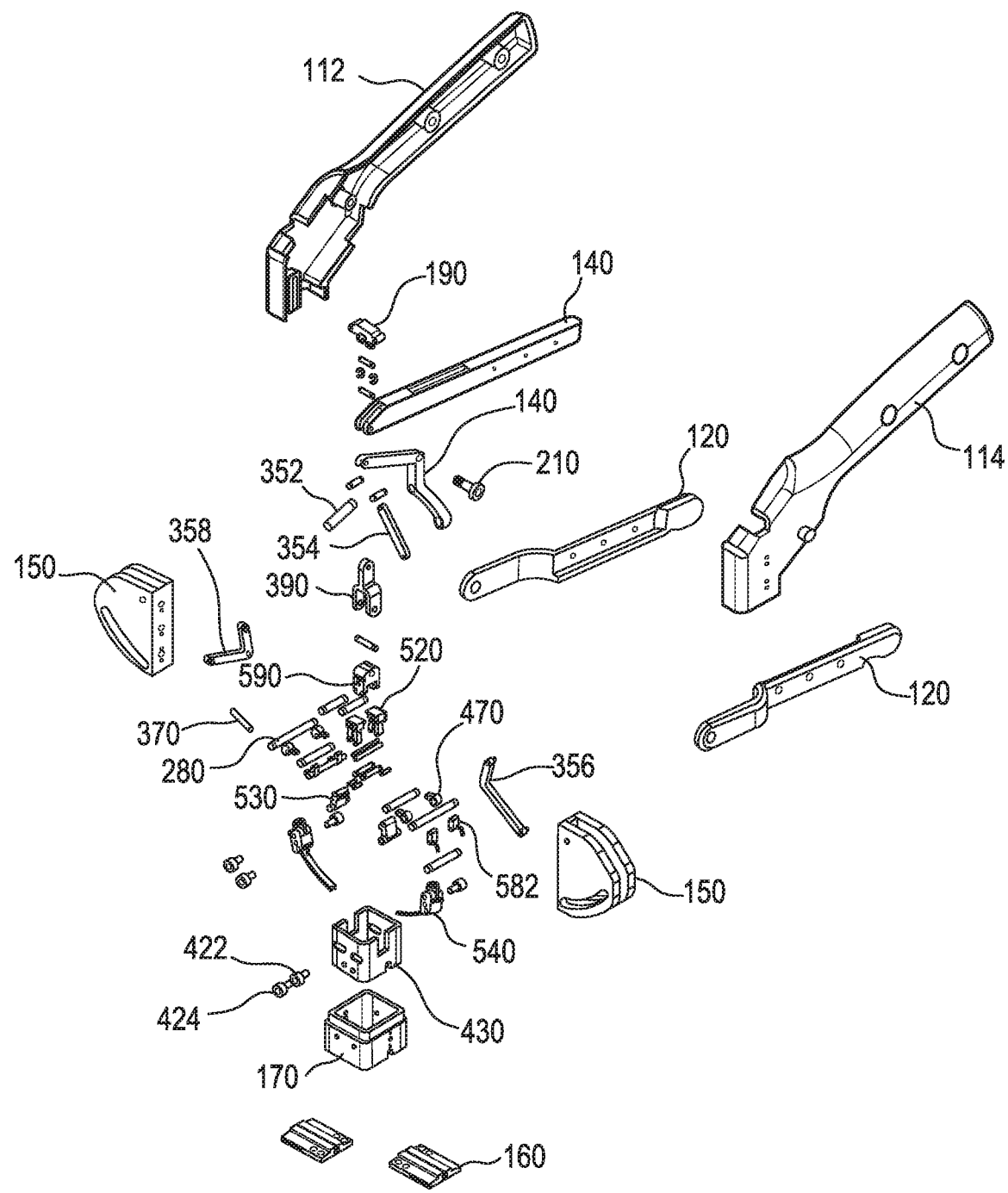
FIG. 1B is an exploded perspective view of the fixation instrument of FIG. 1A.

An illustration of one embodiment of a device 100 of the present invention is presented in FIGS. 1A and 1B. The instrument or device is 100 designed to generally look similar to an ordinary skin stapler and to be utilized in somewhat similar fashion. The device 100 consists of a handle element 110 that is sized to fit within the palm of the target user. There is a tissue engagement trigger 120 that is controlled by the finger grip of the user. Additionally, there is a firing trigger 140 that is depressed upon completion of the stroke of the tissue engagement trigger to deploy the stylus units. The firing trigger is mounted within a slot located in the slotted support bar within the tissue engagement trigger. The two triggers are pivotally attached to the handle element through the use of the pivot pin 130. The handle element 110 includes a main housing 180 portion which serves as the functional rigid structure of the instrument. The handle element is sized to fit within the palm of the user. The axle housing 170 is mounted to the distal face of the main housing element 180. On the two opposing lateral portions of the main housing element 180, two driver cam guides 150 are attached as illustrated. Alternatively the device may only have one driver cam guide. A feeder plate 160 is attached to the base of each driver cam guide element. It can be seen that the distal tip of the firing trigger 142 is in slidable and pivotable engagement with the linkage saddle 190.

Referring to FIG. 2, a view of a partially disassembled device 200 of the embodiment 100 illustrated in FIG. 1A is presented to aid in the description of the various components of the specific embodiment 100. The handle 110 and housing elements have been removed from the illustration for clarity of viewing the various components. The tissue engagement trigger 120, in the prototype form shown, is comprised from three major components that are fastened together, the left trigger half 246, the right trigger half 244, and the slotted support bar 230. While the trigger 120 has been shown as three assembled components, it should be understood that other embodiments may be produced by any alternative conventional means including machining, injection or compression molding, casting, etc. to produce a single unitary structure. The tissue engagement trigger 120 is mated to the firing trigger 140 wherein the distal end of the firing trigger 140 is passed through the slotted support bar slot 220 and the firing trigger 140 is pivotally attached to the to the handle element 110 through the use of a threaded fastener 210. While the embodiment illustrated utilizes cross pins 282, 284, 286, 287, 287, 288 and others as shown, the function of the various cross pins is to provide an axis of relative rotation for each specific part that his held in proximity to the mating part. This functionality in a final device can be achieved in other conventional manners such as through the use of bosses, pins, slots and curved ribs and or receiving features, etc. Each driver cam guide 150 is produced with two opposing wall support structures 262 and 266 which are connected through the use of a back span member 264. Each wall support structure is produced with a curvilinear feature, a slot 260 in this embodiment on opposing sides. It can be seen that the axle housing 170 is produced with a stepped feature 270 to enable the proximal end of the axle housing 170 to fit within the distal end of the main housing element 180. The ends of the two axle shafts 280 are visible and are pivotally engaged with the axle housing 170 and are engaged at opposite ends with the axle housing element.

Referring to FIG. 3, the partially disassembled version 300 of the embodiment 200 of FIG. 2 is illustrated without one of the driver cam guides 150 and opposing wall support structures 262 and 264 to enable the visualization of the components typically assembled within this feature. The slot 350 in the distal end of the firing trigger 140 is shown. The slot 350 enables the slidable linkage with the center portion of the driver saddle element 190. The two lateral ends of the upper portion of the driver saddle are in pivotable engagement with two linkage bars 352 and 354. The two linkage bars 352 and 354 are in pivotable engagement with the upper ends of the acute link elements, 356 and 358. Additionally, the distal end 310 of the tissue engagement trigger slotted support bar is in pivotable engagement with the upper portion 394 of the driver yoke 390. The lower portion of the driver yoke 392 is formed in the shape of a "Y" to receive its mating component. The tissue fastener 370 is seen to be located within a track feature 380 in the feeder plate. The fasteners 370 may be fed in from the side of the feeder plate or from a spring loaded magazine located on top of the feeder plate not shown. The fasteners 370 when in the track 380 of the feeder plate are positioned to be engaged upon the compression of the firing trigger.

Referring to FIG. 4, a partially disassembled version 400 of the embodiment 300 illustrated in FIG. 3 is provided. The axle housing is not present and the inner retractor housing 430 is shown. The device 400 includes four retractor housing cam levers 470, only one is labeled. The cam levers 470 are pivotally engaged to retractor housing through the location within the retractor housing slots 440. The opposite ends of the cam levers are pivotally engaged with their respective mating components. The retractor housing is produced with two opposed slots one of which is labeled 410. The slots 410 provide the necessary clearance to enable the retractor housing to be slidable vertically within the mating axle housing 170 element. The lower end of the acute linkage element 356 is in pivotable engagement with the stylus mount 420. The stylus mount 420 has two cam glide bearings 422 and 424 mounted to the opposite sides of the stylus mount 420. It can be seen that the cam glide bearings 422 and 424 provide for slidable engagement with the driver cam 150 guide elements. While these elements are illustrated as mounted components, it is envisioned that the functionality cam glide bearings can be provided through the use of raised boss pin or other mating curvilinear features that are reciprocal in shape with receiving features on the driver cam element.

Referring now to FIG. 5, a partially disassembled version 500 of the embodiment 400 detailed in FIG. 4 is provided. The balance of the linkage attachments will be detailed. The driver yoke is attached to the pivot base 590. The upper ends of four cam linkage bars 520 are pivotally attached to the pivot base 590 through the use of pins that are passed through the first pair of cam linkage bars 520 through the pivot base unit and through the second pair of cam linkage bars 520. The pins are longer than the width of the two pairs of cam linkage bars 320 and the pivot base unit. The extended ends of the pins are passed into pockets in the two opposing pivot base cap plates 510 that are fixedly attached to the pivot base. The opposite ends of the cam linkage bars 320 are pivotally attached to the cam lever extensions 594. The device is seen to have four tissue hook base elements 580. The tissue hook base element 580 is produced in an "L" shaped configuration. The thickest portion of the tissue hook base element 580 serves as a driver and attachment point for the tissue hook 582 and links the hook to the axle shaft 280. The tissue hook 582 in the illustrated embodiment is square in profile with a pointed distal end for piercing tissue and is integral to the tissue hook element 580, however, the tissue hook 582 may be produced of various geometric profiles such as cylindrical, triangular, hexagonal etc., and may be produced as a discrete element that is fixedly attached to a base or linkage element. The tissue hook base element 580 is mounted to the axle shafts 280 and 282 in opposing directions lateral of the midline of the device. The center portions of the axle shafts 280 are ideally situated at the center of the wide driver linkage elements 530, two of which are utilized in the device. The upper portions of the wide linkage elements 530 are pivotally attached to the lower portion of the pivot base element. The stylus mount 420 is produced with a thick center region 540 which is produced with threaded receiver holes into which the cam glide bearing elements 422 and 424 are threaded.

Figure 6:
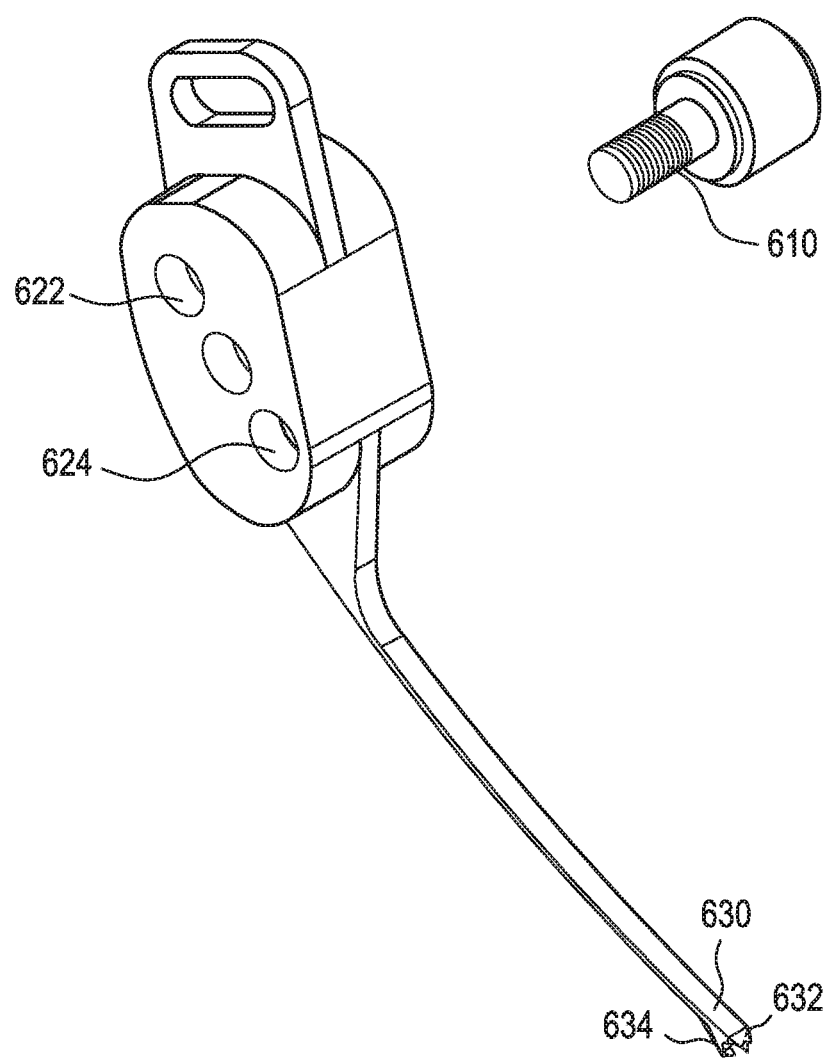
FIG. 6 is a magnified perspective view of the stylus.

Referring to FIG. 6, a magnified, close-up illustration of the stylus 420 is presented. The stylus thick center region 540 is shown with the threaded holes 622 and 624 to receive the threaded extension of the cam bearing shaft 610. It should be noted that alternative configurations of the stylus body are possible that may utilize molded, machined, inserted type features to provide the same guiding functionality of the cam glide bearings. The leading end of the stylus 630 has been produced with a receiving pocket 634 for a mating feature on the leading end of the fastener. The surrounding portions 632 of the leading end of the stylus 420 are also tapered. The leading tip of the fasteners are produced with a mating taper to ensure a smooth transition to the stylus tip and thereby facilitate a smooth dilation of the tissue as the fastener is forced through the dermal tissue.

The functionality of the previously described elements will be described further. The first stage of operation involves the depression of the proximal end of the tissue engagement trigger 120 towards and partially into the handle element 110. As this depression occurs, it causes the handle 110 to rotate about the pivot pin 130 and the distal end of the tissue engagement trigger 120 moves downwards towards the axle housing 170. The distal tip of the tissue engagement trigger 120 forces the driver yoke 390 downwards towards/ into the axle housing 170. The motion of the driver yoke 390 forces the pivot base 590 downward and the two cam linkage bars 520 against the cam lever extensions 594. Since the cam levers 440 are mounted to axle shafts 280 which are in a laterally fixed but rotatable position within the axle housing 170, the cam lever extension rotates downward and laterally away from the mid-line of the instrument 100. This rotation causes the eccentric portions of the cam lever elements to rotate the thicker portion of the eccentric region upwards into the upper portion of the retractor housing slots 470. This motion causes the retractor housing 430 to lift upwards within the axle housing 170. Since this motion occurs as the result of a cam action, the housing 170 can be lifted at a relatively low rate of upward displacement during the initial part of the instrument stroke and then produce a greater rate of upward displacement as the cam lever continues to rotate. In addition to the motion of the retractor housing, the same downward stroke of the pivot base forces the wide driver linkages 530 to rotate about their respective pivot pins. This rotation of the pivot pin causes the tissue hook base elements 580 and associated tissue hooks 582 to rotate initially downward out of the face of the axle housing 170 and inwards towards the midline of the instrument 100. The relative motion of the retractor housing element with the pivot shafts moving away from the lower surface of the axle housing 170 produces a lifting effect of the tissue hook element relative to the fixed axle housing 170. Once the stroke of the tissue engagement trigger 120 has reached the stop position, the proximal end of the firing trigger 140 is depressed towards the handle element 110. This depression of the proximal end 141 of the firing trigger 140 causes the distal tip 142 of the element to rotate about the pivot pin in a downwards direction. The downward motion of the distal tip 142 of the firing trigger element forces the linkage saddle 190 downwards and consequently forces the linkage bars 352 and 354 downwards. As the linkage bars 352 and 354 are in pivotable engagement with the linkage saddle 190, the opposing end is in pivotable engagement with the top of the acute link elements 356 and 358, the top of the acute link element is forced laterally away from the midline of the instrument 110. This outward lateral motion of the top of the acute link element forces the lower portion acute link element to rotate about its pivot pin and results in an inward motion, from lateral to midline, of the distal tip. Since the distal tip is engaged with the slotted portion of the stylus, it translates this motion into the stylus unit which is guided through an arcuate path, controlled by the fit of the cam guide slots and the cam bearings. The instrument 100, as illustrated, passes the two opposing stylus tips, and associated fasteners, in an offset, approximately 4-5 mm, position relative to each other. In use this motion will provide counter lateral pressure to the tissue during the opposing fastener deployment. Additionally, the illustrated embodiment 100 passes the two opposing stylus units within the tissue boundaries defined by the two pairs of opposing tissue hook elements. Once the firing trigger 140 has been depressed and the fastener delivered, the firing trigger 140 is released and then the tissue engagement trigger 120 is released. This disengages the instrument 100 from the tissue and a new fastener is positioned in the track feature 380 of the feeder plate. While the magazine for fastener delivery is not illustrated, it can be seen that a magazine that is either coil fed, or containing discrete fasteners, may be utilized in conjunction with the instrument 100.

Figure 7:
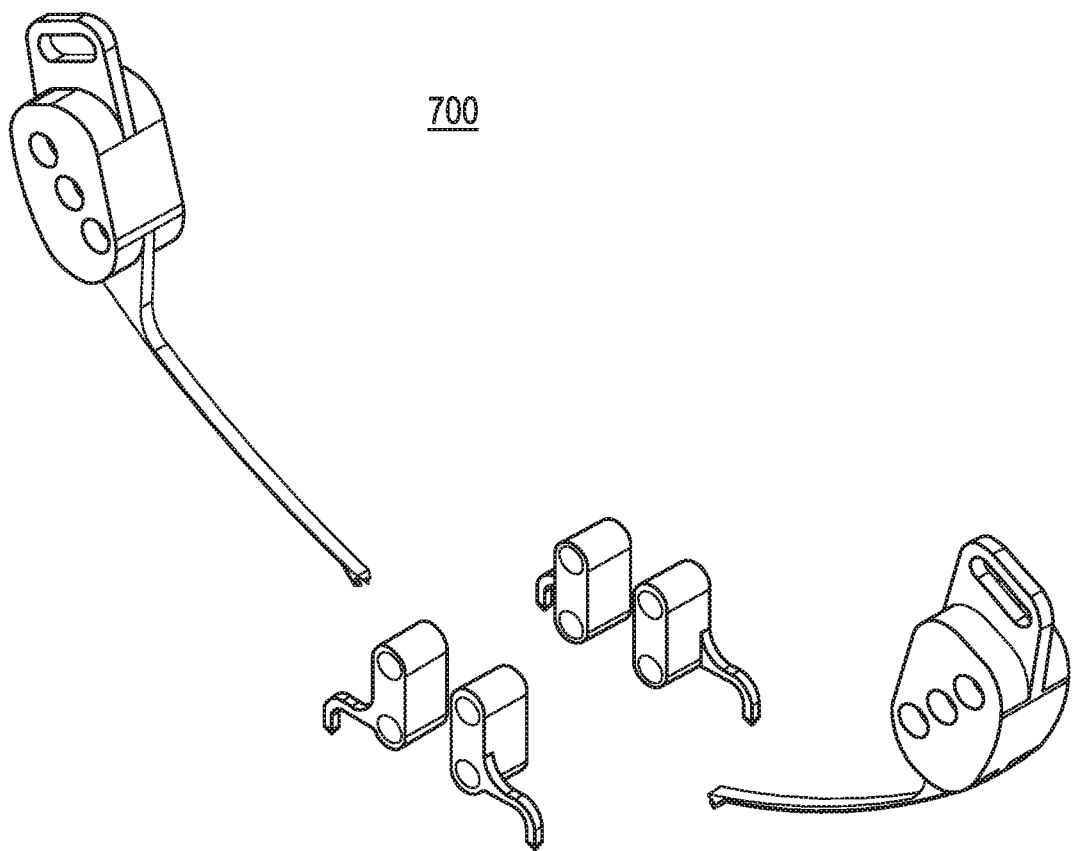
FIG. 7 is a perspective view showing the components of the instrument of FIG. 1A that pierce tissue; in particular, showing the respective positioning of the tissue hook base elements and the stylus units.

Referring to FIG. 7, only the components that pierce the tissue 700 are illustrated. The components are positioned in the proper location with the balance of the mating components of the instrument not shown. The four tissue hook base elements 580 are arranged into two pairs of opposing elements. The two opposing stylus units 420 are positioned in offset opposing positions. It can be seen that the two stylus units 420, when driven to the piercing position, would lie within the tissue segment captured between the four tissue engagement hook base elements 580.

Figure 8:
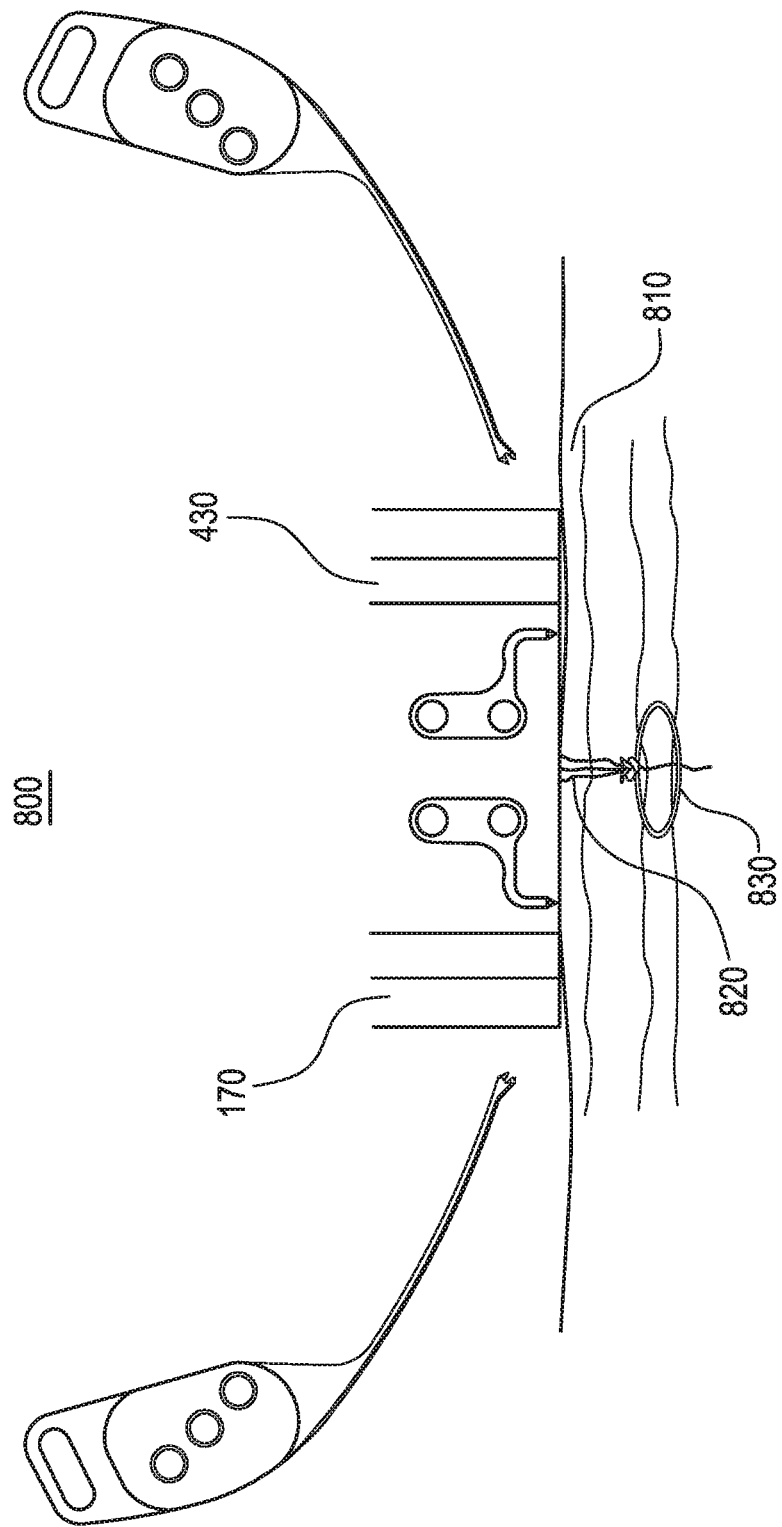
FIG. 8 is a partial side view showing the stylus units, tissue hook base elements, inner retractor housing and axle housing adjacent to the dermal layer of tissue.

Referring to FIG. 8, a partial sectional view 800 of the stylus units 420, the tissue hook base elements 580, inner retractor housing 430 and axle housing 170 is illustrated. The distal face of the instrument 100 is placed in abutment with the dermal surface 810. The distal face of the instrument 100 is formed by the lower surface of the axle housing 170 and the inner retractor housing 430. It can be seen that the tissue hook base elements 580 are in the home position with the tissue hook perpendicular to the surface 810 of the dermal layer. A partial gap 820 in the wound edges to be joined and is located anterior to the suture 830 in the fascial layer.

Figure 9:
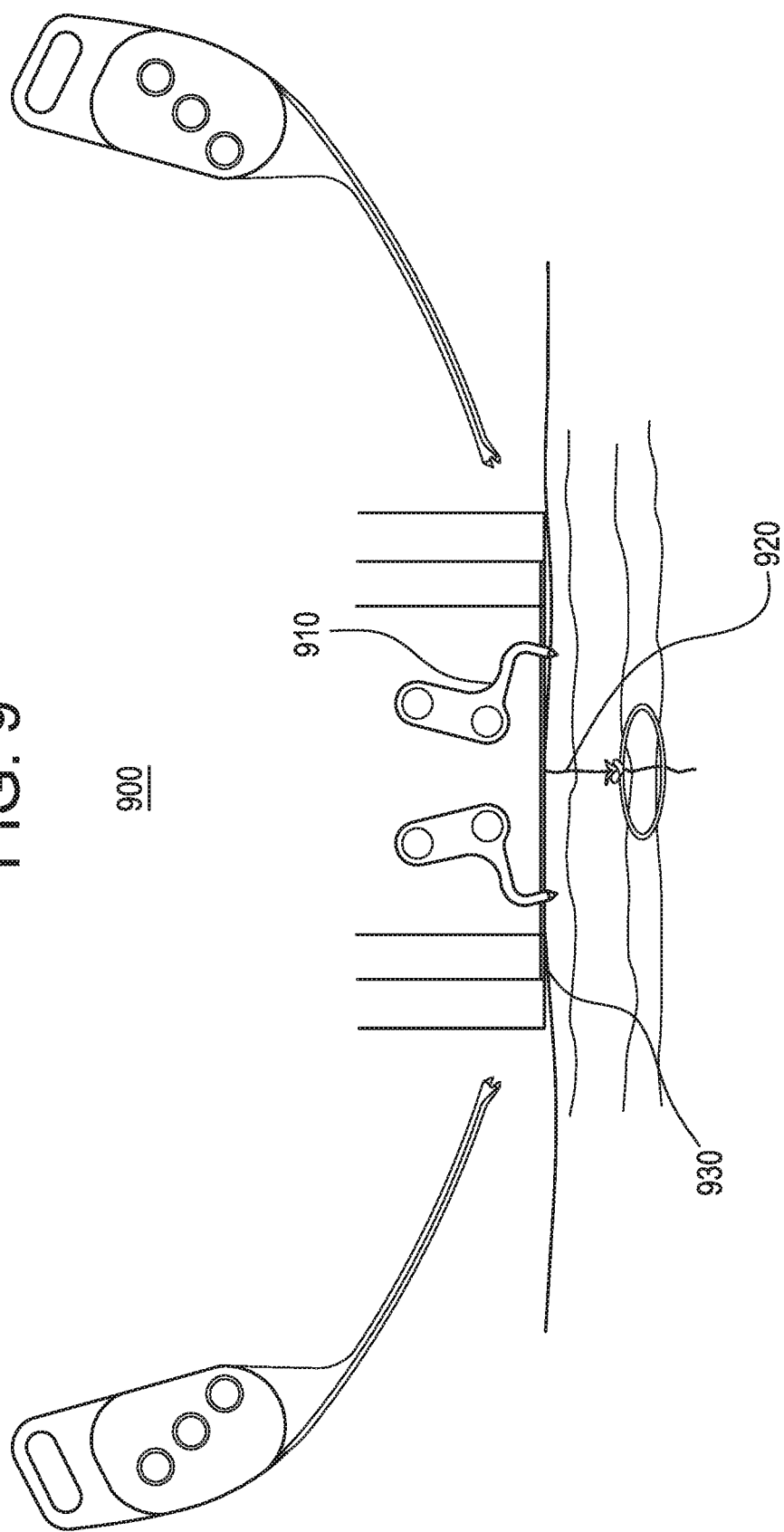
FIG. 9 is a partial side view showing the tissue engagement trigger partially depressed; partial rotation of the tissue hook elements causes the tips of the tissue hooks to pierce tissue and draw the wound edges closed.

Referring to FIG. 9, the partial sectional view of the embodiment is 900 is illustrated with the tissue engagement trigger 120 partially depressed. In the partially depressed position, the cam bearings are rotated into slight engagement with the retractor housing 430 which causes slight elevation of the retractor housing 430 and the formation of an associated gap 930 between the surface 810 of the dermis and the face of the retractor housing 430. Additionally, the partial downward stroke of the tissue engagement trigger 120 results in the partial rotation of the tissue hook base elements 580 which produces an angular displacement 910 of the "L" shaped tissue hook. As a result of the angular displacement of the cantilever "L" shape, the tips of the tissue hooks pierce the tissue and draw the wound edges 920 closed.

Figure 10:
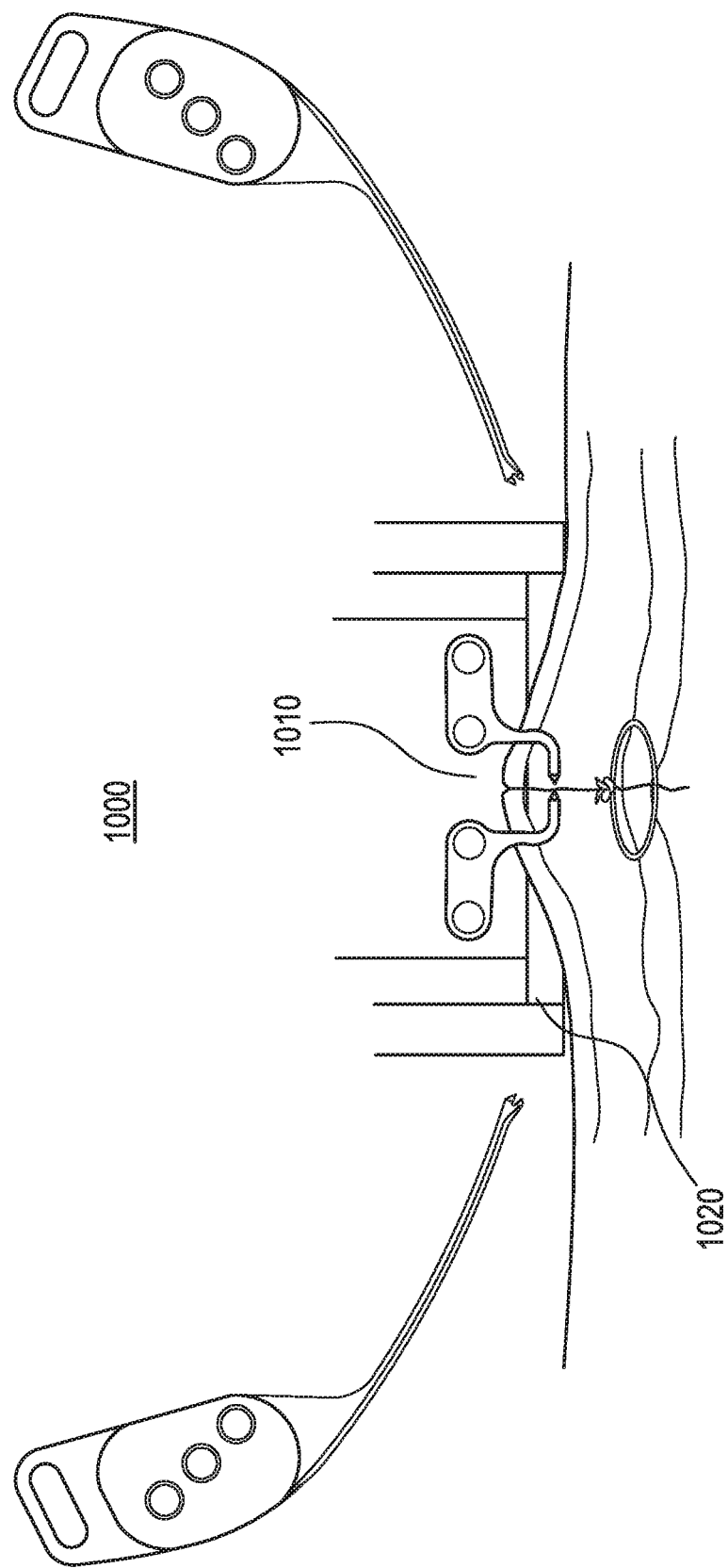
FIG. 10 is a partial side view showing the tissue engagement trigger fully depressed with the retractor housing fully retracted and the tissue hook base elements fully rotated and engaging the dermal layer and everting the tissue edges.

Referring to FIG. 10, the partial view of the embodiment 1000 is illustrated with the tissue engagement trigger 120 fully depressed. In this position, cam bearings are fully rotated approximately 90 degrees which causes a full engagement with the retractor housing 430. In this position, the retractor housing 430 is fully retracted thereby providing a gap 1020 for the tissue to be approximated to be pulled upwards relative to the face of the axle housing 170. The tissue hook base elements are fully rotated approximately 90 degrees and provide a lateral clamping and compression of the tissue edges as well as a natural eversion of the edge of the dermal layer due to an over compression of the tissue and the associated volume shifting of the tissue to accommodate the clamping. In this position, the axle housing 170 is actually providing a counter traction to the dermal layer to provide an elevated tissue target for piercing and securement as well as an everted tissue 1010 approximation.

Figure 11:
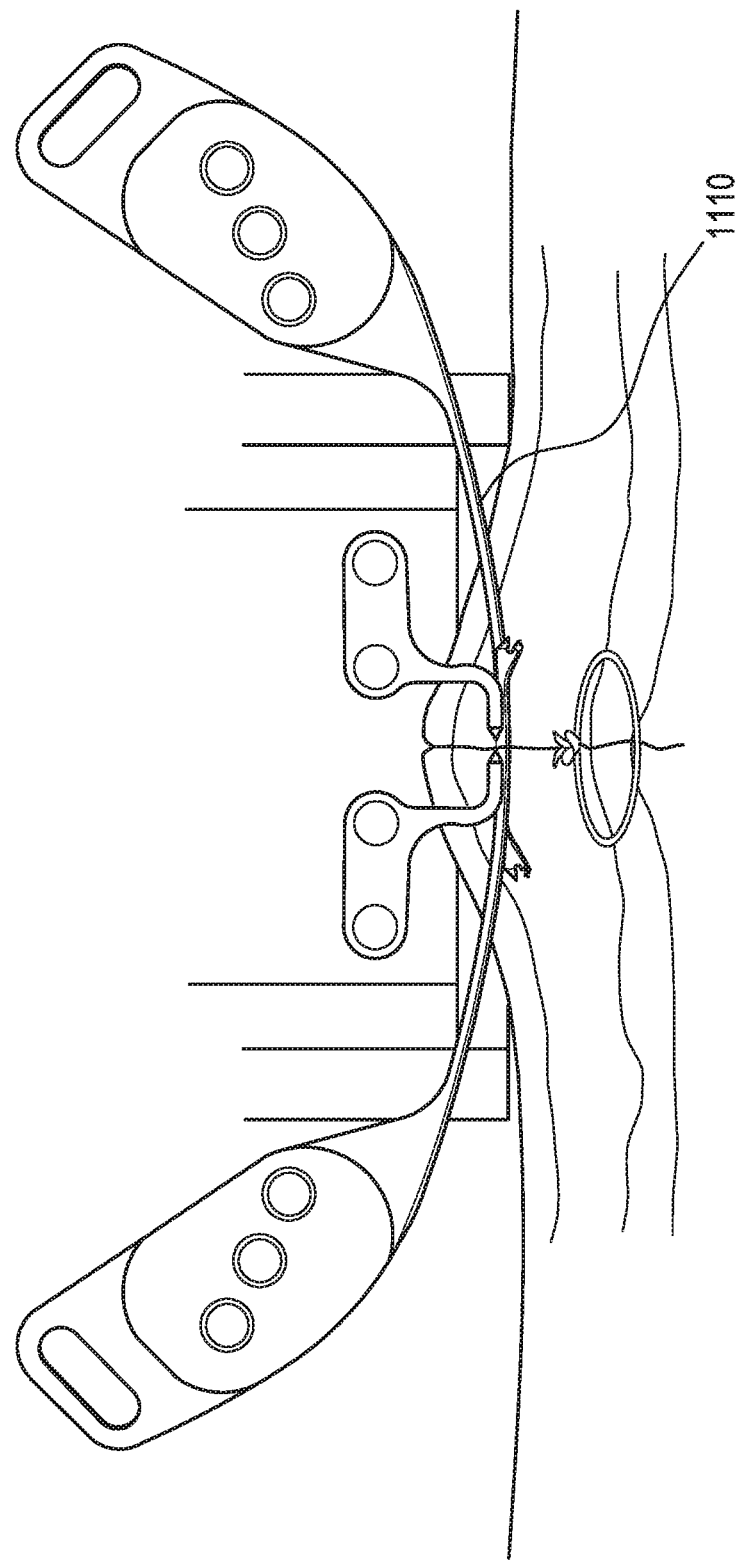
FIG. 11 is a partial side view showing each deployed stylus buried within the target tissue after travelling a full stroke.

Referring to FIG. 11, a partial view of the embodiment 1100 is illustrated with the firing trigger in the depressed position. The deployed stylus 1110 is shown buried within the target tissue after is has pierced the tissue and travelled its full stroke. The leading edge of the stylus has engaged with a fastener 370, not shown, that is captured by its leading edge in the feeder plate 160, and has passed it through the dermal layer.

Figure 12:
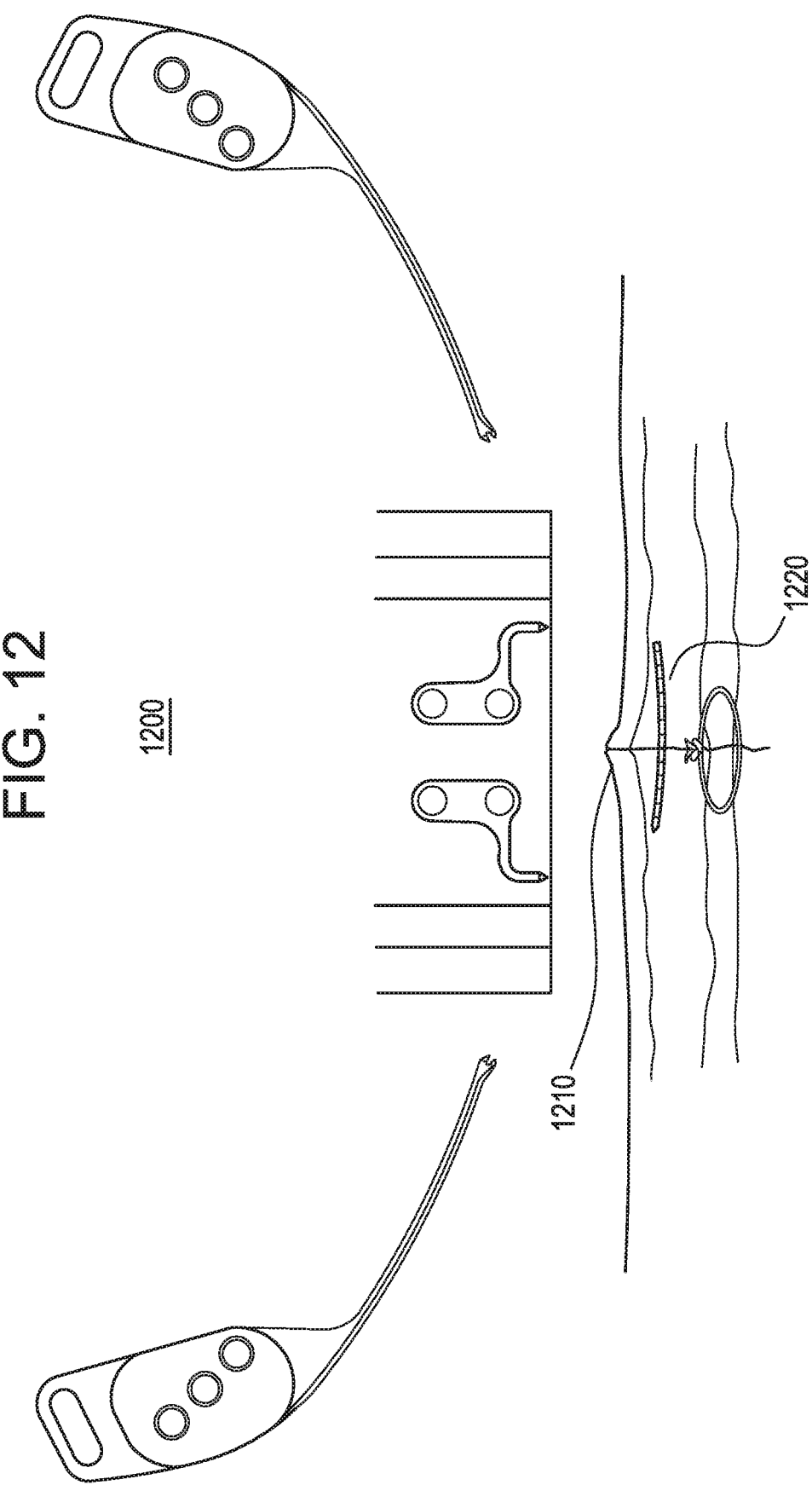
FIG. 12 is a partial side view showing the instrument in the post-firing condition with a tissue fastener deployed in tissue and the instrument lifted away from the dermal layer.

Referring to FIG. 12, the partial view of the embodiment 1200 is shown in the post firing condition where the firing trigger and tissue engagement trigger have been released and the instrument face has been lifted away from the dermal layer. The wound edge is in approximation with an everted edge 1210. Additionally, the deployed fastener 1220 can be seen within the dermal tissues. While the fastener 1220 is placed in an arcuate path that is defined by the arc of the stylus, the fastener 1220 tends to flatten out slightly as the tissue engagement hooks are released from the tissues. As the tissue loading on the tissue engagement hooks is decreased during trigger release, the loading is transferred to the fastener element 1220. This transfer of loading is accompanied by a slight lateral motion of the tissue away from the midline of the approximated wound edges. This motion of the tissue ensures that the fastener 1220 is seated or fully engaged with the tissues. Unlike instruments that drive a fastener through the tissues without the over compression provided by the tissue engagement hooks, the wound does not gap after load transfer as the midline compression and translation of the tissue prior to the firing of the fasteners 1220 compensates for any tissue elasticity and compliance effects.

Figure 13:
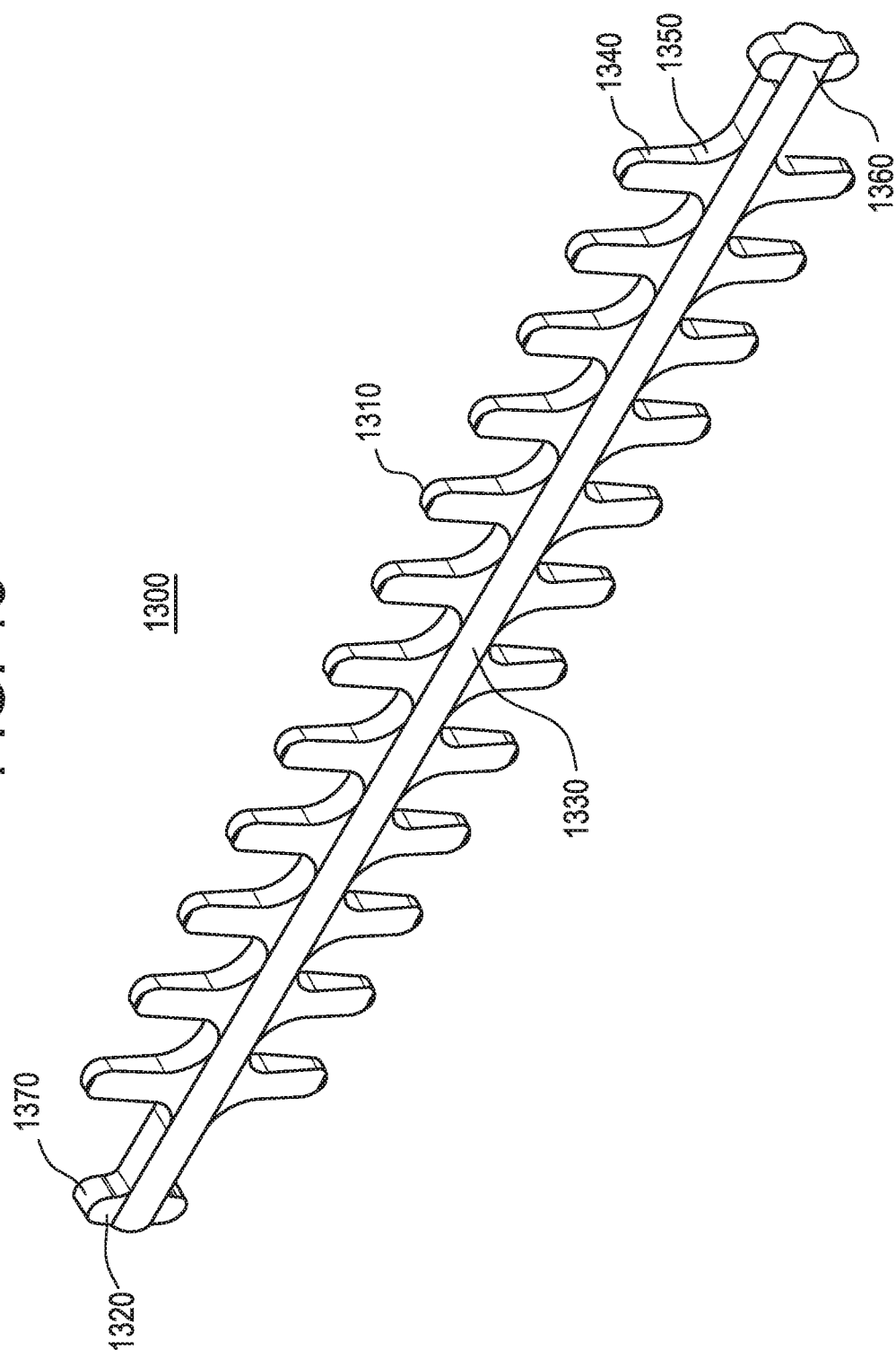
FIG. 13 is an orthogonal (perspective) view of a non-directional fastener useful with the novel tissue fixation instruments of the present invention.

Referring to FIG. 13, an orthogonal view of a non-directional fastener 1300 is provided. The use of non-directional fasteners inhibits motion of the fastener within the tissues in either direction as opposed to directional fasteners that resist motion in one direction only. The fastener element 1300 may be produced through typical means including molding, extrusion, machining etc. The fastener 1330 has a central elongated region 1330 that extends between two opposing ends 1320 and 1360. Located on each end of the fastener element 1330 are raised "bump-like" stylus engagement elements 1370. These engagement elements 1370 are sized to fit within the receiver features of the tip of the driver stylus. Additionally, the fastener element 1300 is produced with a series of frictional engagement elements 1310 that are sized to fit within the tissue tract created by the stylus unit. The frictional engagement elements 1310 extend from the central elongated region 1330 in a generally perpendicular orientation. Each frictional engagement element 1310 is produced with a base portion 1350 and a tip region 1340. The cross sectional area of the tip region of the frictional engagement element 1310 is generally smaller than that of the base portion of the same element. This gradual reduction of the cross sectional area results in an element 1310 that has a tip region with a greater flexibility and compliance than that of the base portion, thus if the tips extend beyond the tissue tract during passage, they are able to flex to accommodate any potential tissue drag during installation.

Referring to FIG. 13A, an orthogonal view of a directional fastener 1380 is provided. The fastener 1380 is seen to have an elongated central member 1382 having a distal end 1384 and a proximal end 1386. A plurality of engagement members 1390 extend from opposite sides of central member 1382. The engagement members 1390 have base portions 1392 and tip portions 1394. The engagement members 1390 are seen to be angulated toward the proximal end 1386 with respect to central member 1382.

Figure 14:
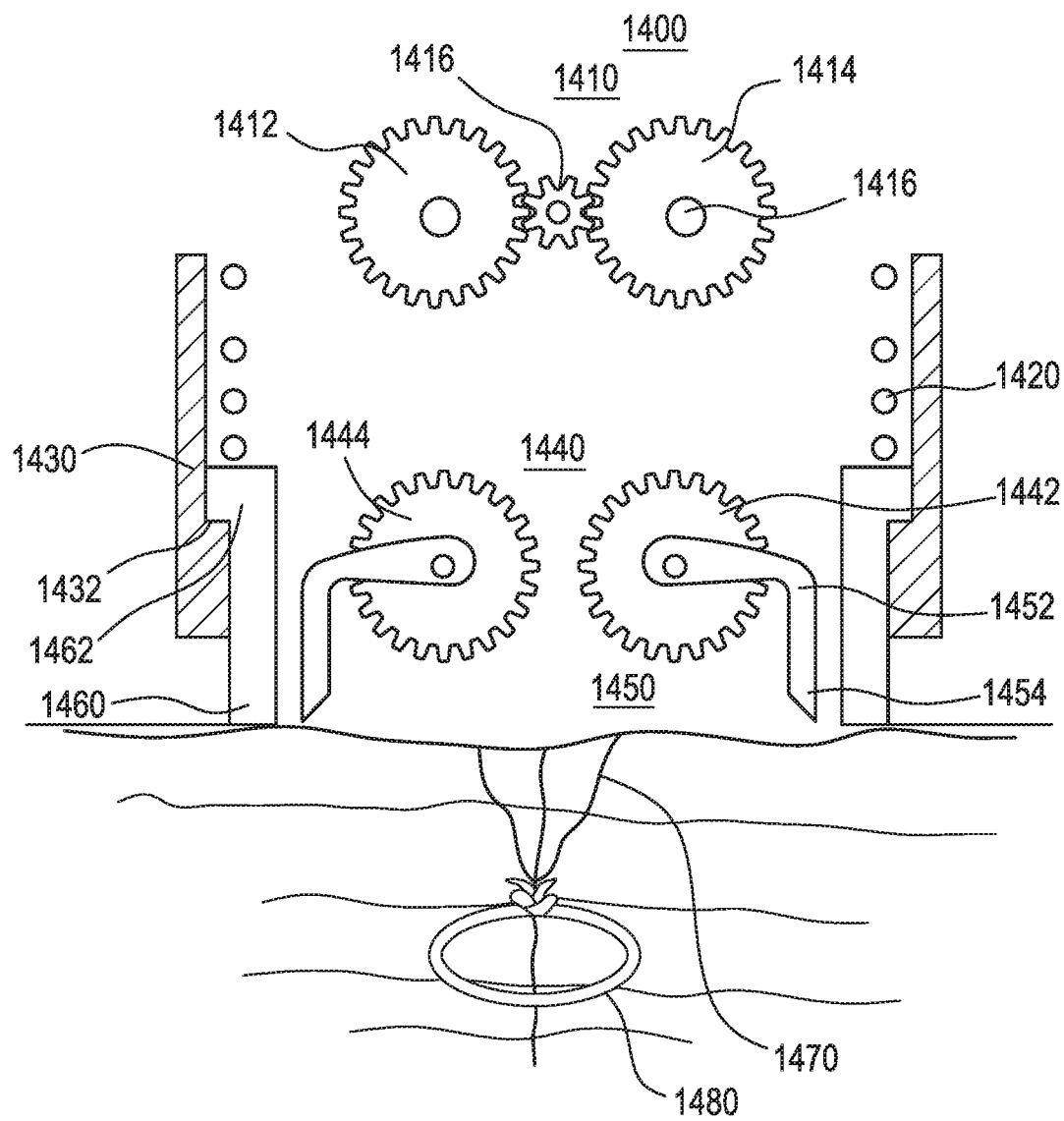
FIG. 14 is a basic partial view of the tissue interface portion of a gear driven embodiment of a tissue fixation device of the present invention.

While the prototype embodiment 100 that has been described utilizes a system of lever driven actions within the instrument, gear driven devices that incorporate linear stylus application of fasteners instead of arcuate drivers are also feasible. Referring to FIG. 14, a basic partial view 1400 of the tissue interface portion of a gear driven embodiment is provided. The tissue margins to be approximated 1470 are slightly gapped. The fascial tissues are secured together through the use of a traditional suture 1480. The device is illustrated with a set of drive gears 1410 that are mated to a rack gear, not shown, that is driven by the tissue engagement trigger, also not shown. There is one central drive gear 1416 that is actuated by the rack gear that is offset from the two oppositional drive gears 1412 and 1414. These chive gears are mounted on shafts 1416 that are contained within a movable housing, not shown. There is a pair of tissue engagement hooks 1444 and 1442. The tissue hooks may be comprised of an extension shaft 1452 and a tissue penetrator 1454 and an integral gear style base with a pocket or through bore for mounting on their respective shafts. The safety shield 1460 extends distally from the gear housing 1430. The use of an extending safety shield enables a pronounced placement of the tissue penetrators and advanced piercing of the dermis when the device is pressed against tissue. This configuration enables a deeper bite within the tissue to increase the elevation of tissue upon completion of the instrument stroke. The safety shield 1460 may be positively driven by direct linkage to the tissue engagement trigger stroke, or alternatively as illustrated with a return spring 1420. The safety shield 1460 is retained within the gear housing 1430 through the use of mating interference features 1432 and 1462. While the embodiment utilizes a stepped interference, other features such as pins, tapered fits, spring plungers, etc. are also feasible.

Figure 15:
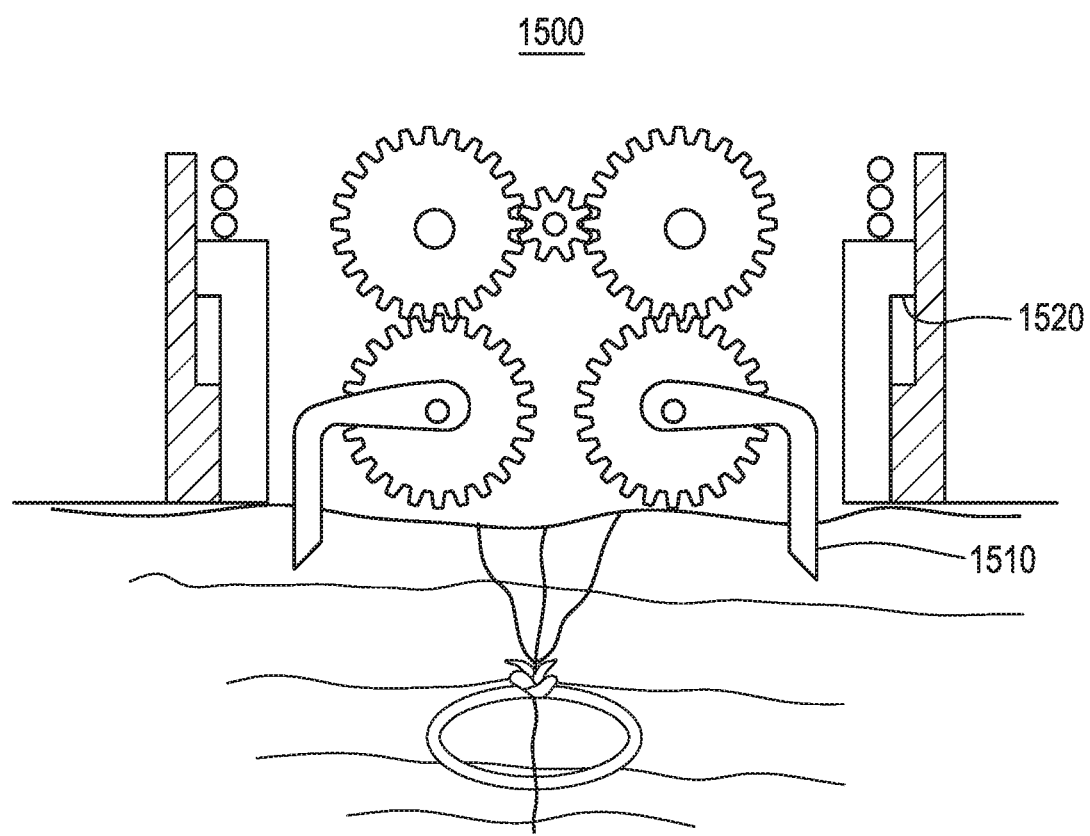
FIG. 15 shows the partial view of the tissue fixation device of FIG. 14 with the safety shield depressed as the face of the instrument is pressed against the dermal layer.

Referring to FIG. 15, the partial view of the embodiment with the safety shield depressed as the face of the instrument is pressed against the dermal layer is illustrated. It can be seen that the tissue has been pierced by the tissue penetrator. Additionally, as the safety shield has retracted, a clearance 1520 has formed between the stop features of the safety shield and gear housing. It should be noted that in this position, the slight gapping of the wound edges remains unaltered as the penetrators are capable of piercing the dermal layer prior to any angular rotation.

Figure 16:
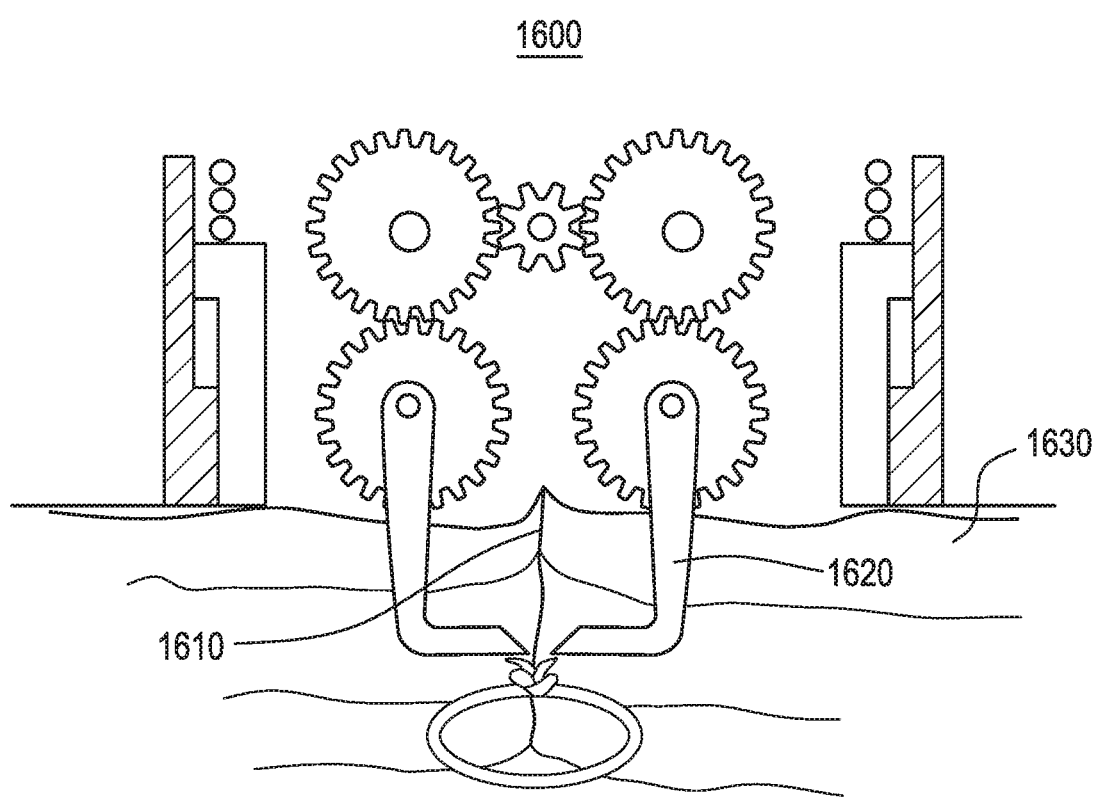
FIG. 16 shows the fixation device of FIG. 15 after the trigger has been fully depressed; in this position the tissue engagement hooks have fully rotated approximately 90 degrees.

Referring to FIG. 16, tissue engagement trigger has been fully depressed. In this position, the tissue engagement hooks have fully rotated approximately 90 degrees. The rotation of the tissue hooks draws the lateral tissue towards the midline of the instrument, thereby causing an over-compression of the wound margin and the necessary eversion 1610 of the wound edge. Additionally, since there was a relatively pronounced piercing depth, coupled with the full 90 degree rotation, this partially lifts the tissue against the face of the safety shield and gear housing.

Figure 17:
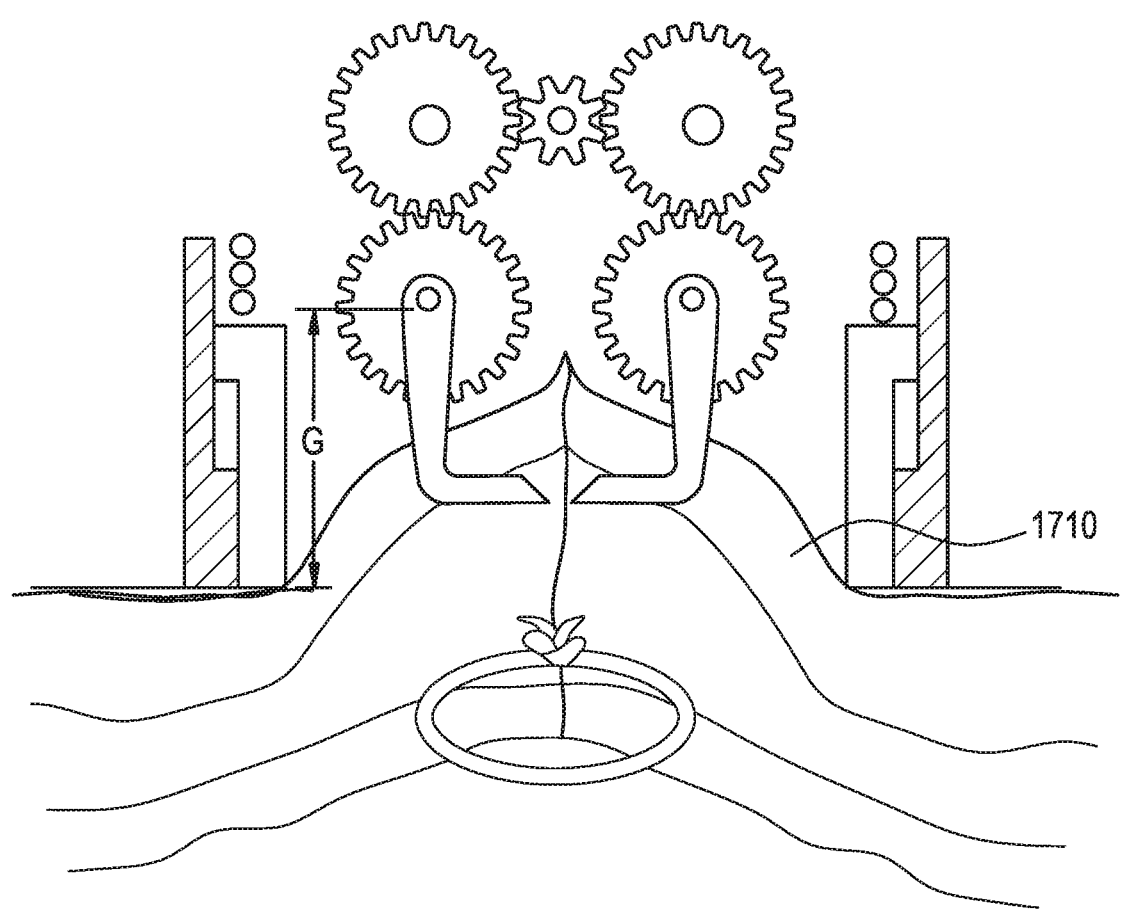
FIG. 17 shows a partial view of the delivery instrument with the firing trigger depressed approximately half of the possible stroke length; during this portion of the stroke, the gear axle housing, not shown, is lifted by a cam shaft which is linked to the firing trigger through a separate rack gear.

Referring to FIG. 17, a partial view of the delivery instrument with the firing trigger depressed approximately half of the possible stroke length is illustrated. During this portion of the stroke, the gear axle housing, not shown, is lifted by a cam shaft which is linked to the firing trigger through a separate rack gear. The balance of the firing trigger stroke does not lift the gear train any higher as the cam surface is a constant diameter for the balance of rotation created by the completion of the stroke of the firing trigger.

This relative motion of the gear axle housing relative to the gear housing and safety shield results in the formation of an elevated region of tissue 1710 captured between the two opposing pairs of the tissue hooks, similar to the lever driven device previously disclosed. This elevated region of the tissue provides a target for the subsequent placement of the fastener.

Figure 18:
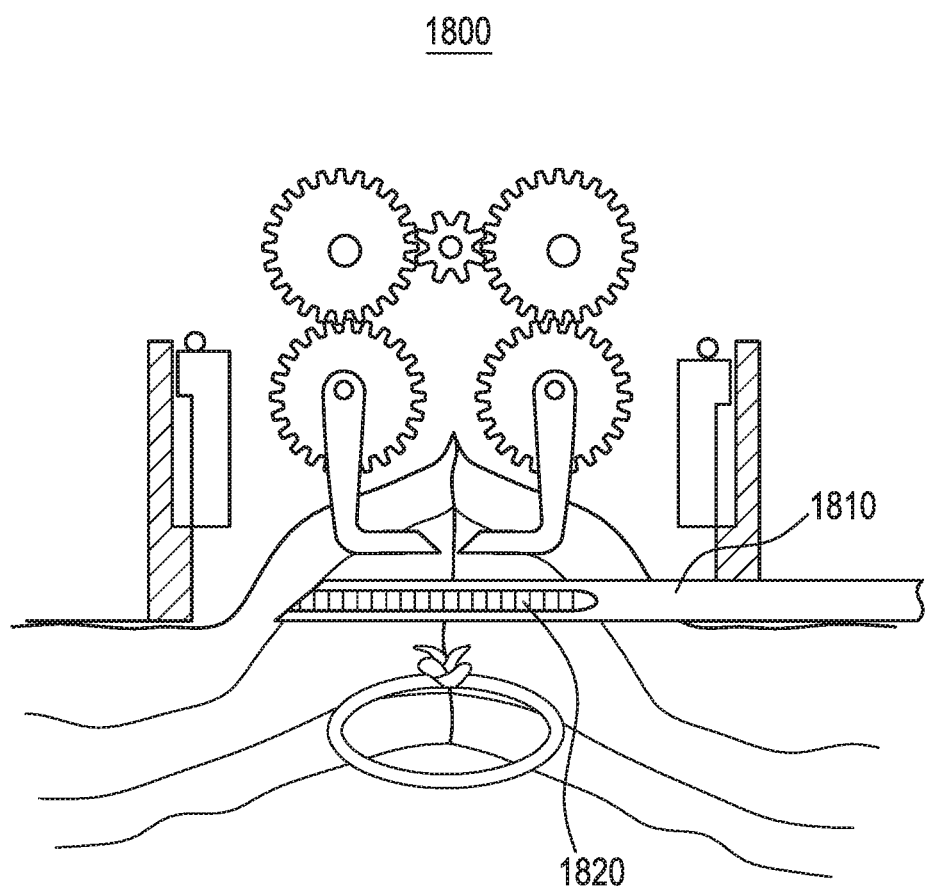
FIG. 18 illustrates the partial view of the device with the firing trigger at the completion of the full stroke 1800.

Referring to FIG. 18, a partial view of the device with the firing trigger at the completion of the full stroke 1800 is illustrated. The firing trigger has engaged with the pull lever portion of the driver system that is connected with the driver shuttle in the delivery stylus housing. This pull lever action results in the lateral motion of the delivery stylus 1810 towards and past the midline of the instrument. Unlike the previously described embodiment, the stylus in this form of the device is relatively linear and does not require an arcuate pathway to penetrate the dermal layer. The frictional drag elements 1820 of the fastener are visible within the track of the stylus.

Figure 19:
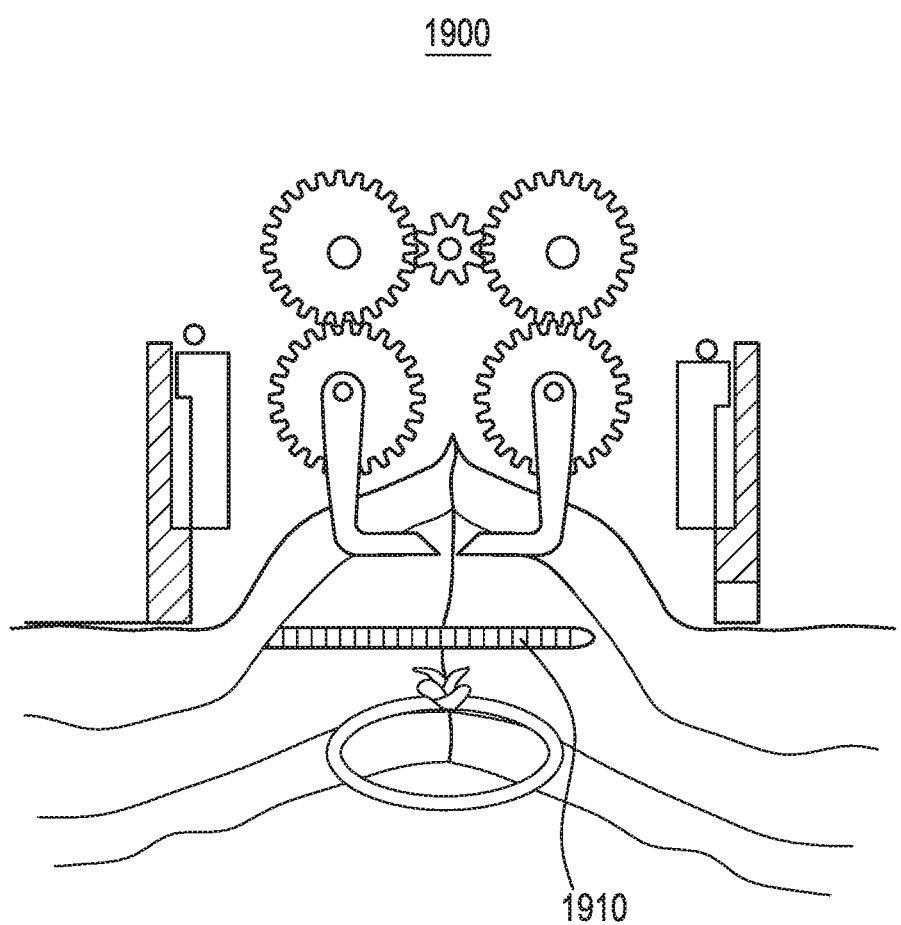
FIG. 19 shows a partial view of the delivery instrument with the firing trigger partially released to position 1900.

Referring to FIG. 19, a partial view of the delivery instrument 1900 with the firing trigger partially released position 1900 is shown. It can be seen that the fastener 1910 remains with the tissue and that the tissue hooks have not yet been released.

Figure 20:
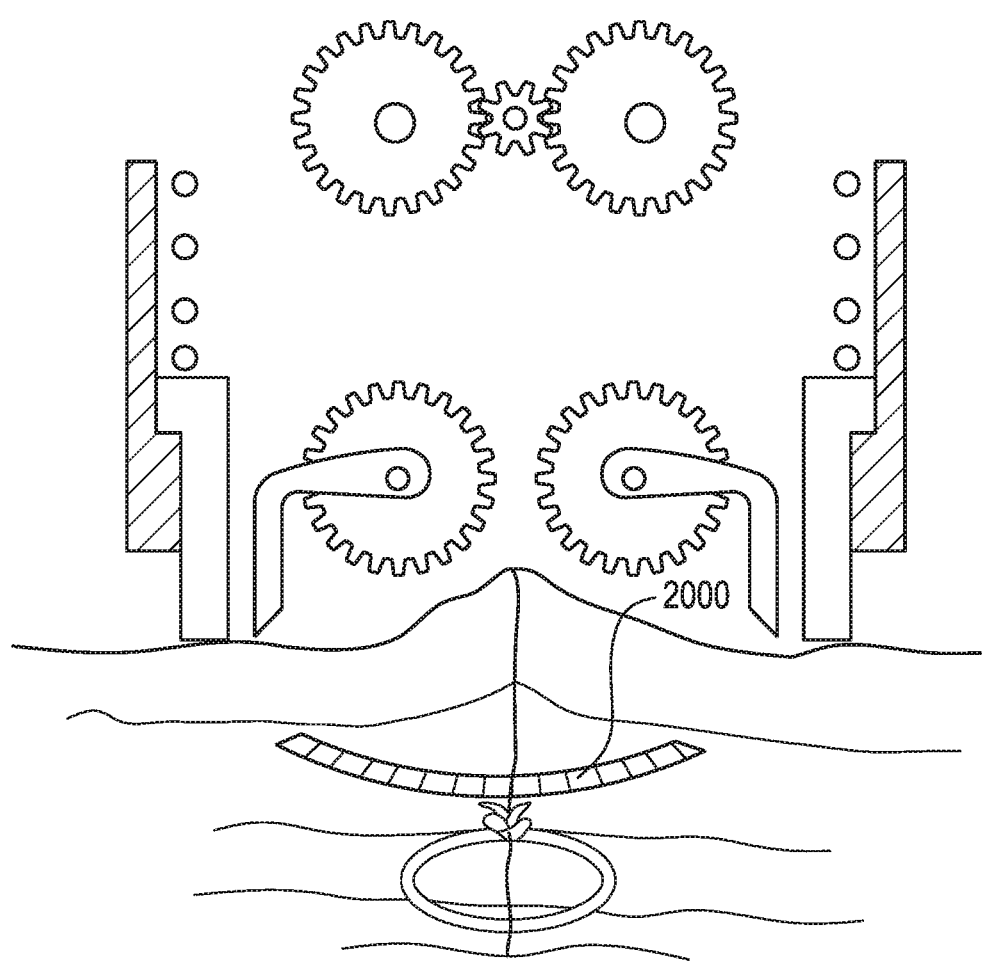
FIG. 20 shows a partial view of the delivery instrument in the fully completed full return position 2000

Referring to FIG. 20, a partial view of the delivery instrument in the fully completed full return position is shown. It can be seen that the tissue that was formerly elevated has been released and has settled back into a normal position. As the tissue resumes the proper vertical positioning, the fastener will flex to form a partially arcuate form 2001. The modification of the fastener due to the flexure may present the opportunity for the use of fasteners with unique cross section features as opposed to the previously disclosed non-directional fasteners illustrated in FIG. 13.

Figure 21A:
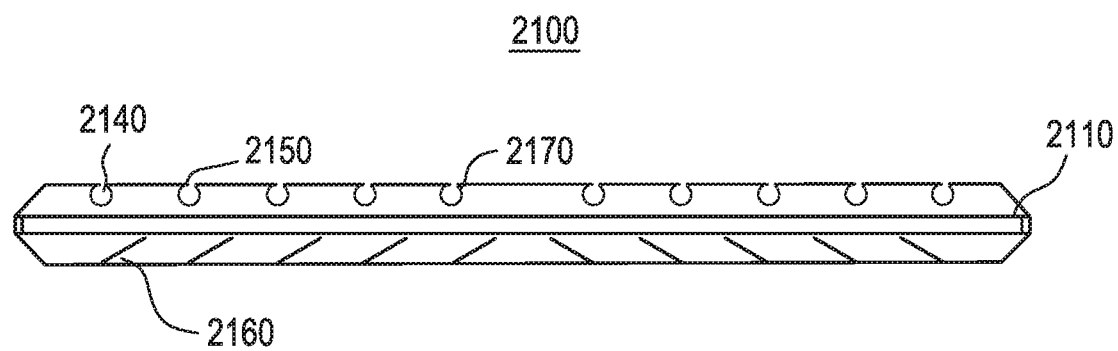
FIGS. 21A and 21B illustrate the side and end views of an alternate fastener 2100 for use with a straight delivery stylus.
Figure 21B:
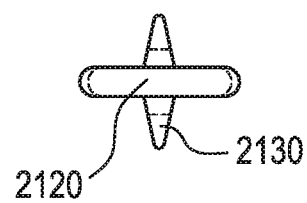

Referring to FIGS. 21A and 21B, the side and end views of an alternate fastener 2100 for use with a straight delivery stylus is illustrated. The fastener 2100 is produced with a central core 2120 that extends between the proximal end and distal end of the fastener. The profile of the fastener 2100 is generally cross-like or "t" shaped. The central core region 2120 is produced with engagement features 2110 located at each end of the fastener, thereby forming a symmetrically shaped fastener. Extending laterally from the central core region 2120 are two extension webs that are generally tapered in profile 2130. The fastener 2100 includes a series of semi-circular cut out features 2140 in one of the web extensions. In this particular embodiment, the feature 2140 is produced with a partially formed circle with a perimeter portion that is blended into a straight extension 2170 to form the open area in the web. In this manner, the edge of the web that results is an opening with an acute angular point 2150 and an opposing point of a less acute angle. This geometry enables the formation of an asymmetric feature that will engage more readily in one direction than in the other. Additionally, it should be noted that the partial circular features 2140 are oriented in the opposite directions for each half of the fastener 2100. The opposing web is produced with a series of slits 2160 cut into the web at acute angles relative to the axis of the web. The slits are placed at a 90 degree relative orientation to each other for the two halves of the fastener 2100.

Figure 22:
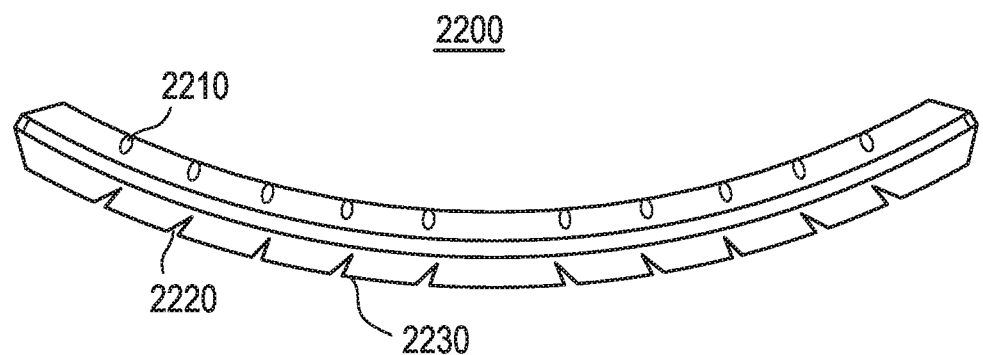
FIG. 22 illustrates the fastener of FIGS. 21A and 21B in the post deployment and loaded condition.

Referring now to FIG. 22, the fastener is illustrated in the post deployment and loaded condition. The loading of the fastener during the release of the tissue hooks from the surrounding tissues results in the fastener becoming altered in shape with a simple bending action. This bending action causes the anterior portion of the fastener to flex inward and to close the semi-circular opening 2210 and thereby biting into the local tissues. The slits that were formed on the opposite web are forced open as illustrated 2220. This opening of the slits exposes the acutely shaped edges of the slits to become exposed thereby enabling engagement with the local tissues. Both of these responses in the fastener due to bending ensure that the fastener remains engaged with the local tissues. While the fastener is illustrated with features that may close upon or pinch the tissues, it may be desirable to form the semi-circular portions with transverse angular cuts that allow the cut surfaces to bypass each other during flexure thereby forcing the acute angled points to extend outward from the web as a traditional barbed suture.

Figure 23:
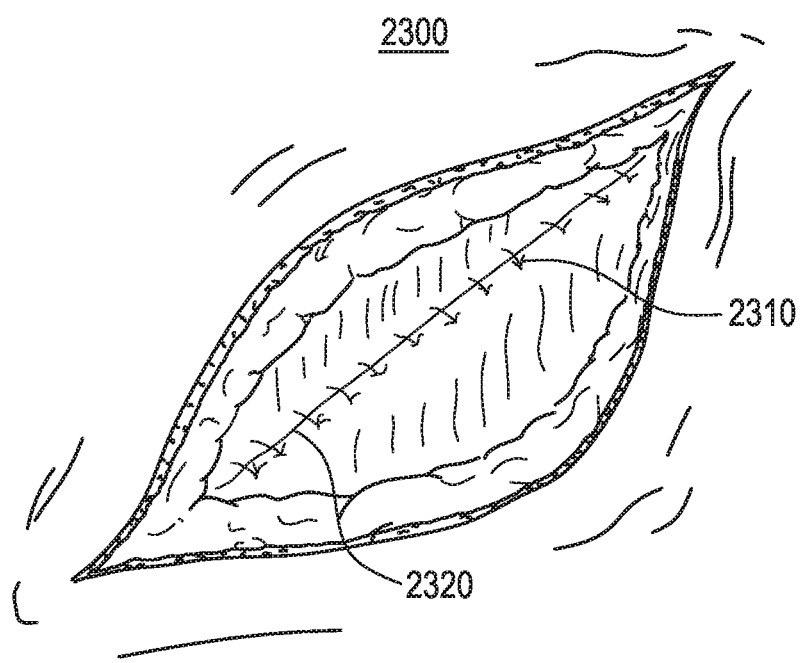
FIG. 23 illustrates a wound within which the deep tissues have been closed through sutures or other similar wound closure devices; the sub-dermal layer is approximated and the wound is not gaping.

Referring to FIG. 23, a wound 2300 within which the deep tissues 2320 have been closed through sutures 2310 or other similar wound closure devices is illustrated. As can be seen, the sub-dermal layer is approximated and the wound 2300 is not gaping.

Figure 24:
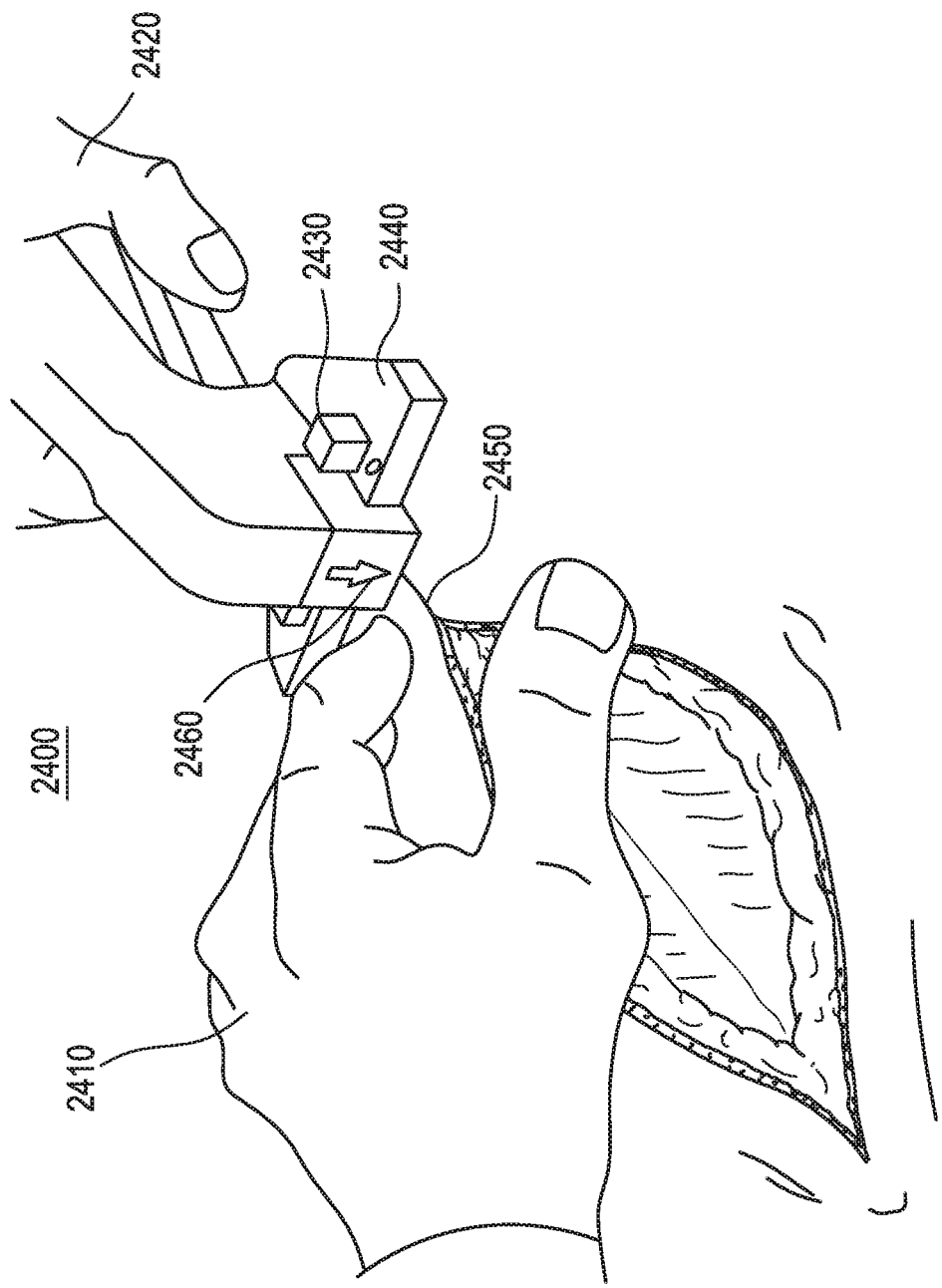
FIG. 24 illustrates the use of a gear driven delivery instrument with the straight stylus of the present invention to approximate the wound.

Referring to FIG. 24, the use of the gear driven delivery instrument with the straight stylus is illustrated. The partially open wound 2400 is held slightly in approximation by the surgical technician's fingertips 2410 through the application of downward pressure and frictional engagement with the skin, as is done with a typical skin stapler.

The center of the delivery device head 2460 is placed across the margins 2450 of the partially approximated wound 2400 and the face of the safety shield is pressed against the surface of the dermis. In this position, the tissue hooks have pierced the dermal layer. The device is operated as previously described by the squeezing the triggers with the opposing hand 2420. Unlike the arcuate delivery system, the stylus housing 2440 is in a plane that is approximately parallel to the tissue being fastened. The spring loaded magazine 2430 is mounted perpendicular to the driver housing and contains the appropriate number of fasteners that are maintained in engagement with the stylus through the use of an internal spring loaded driver mechanism.

Figure 25:
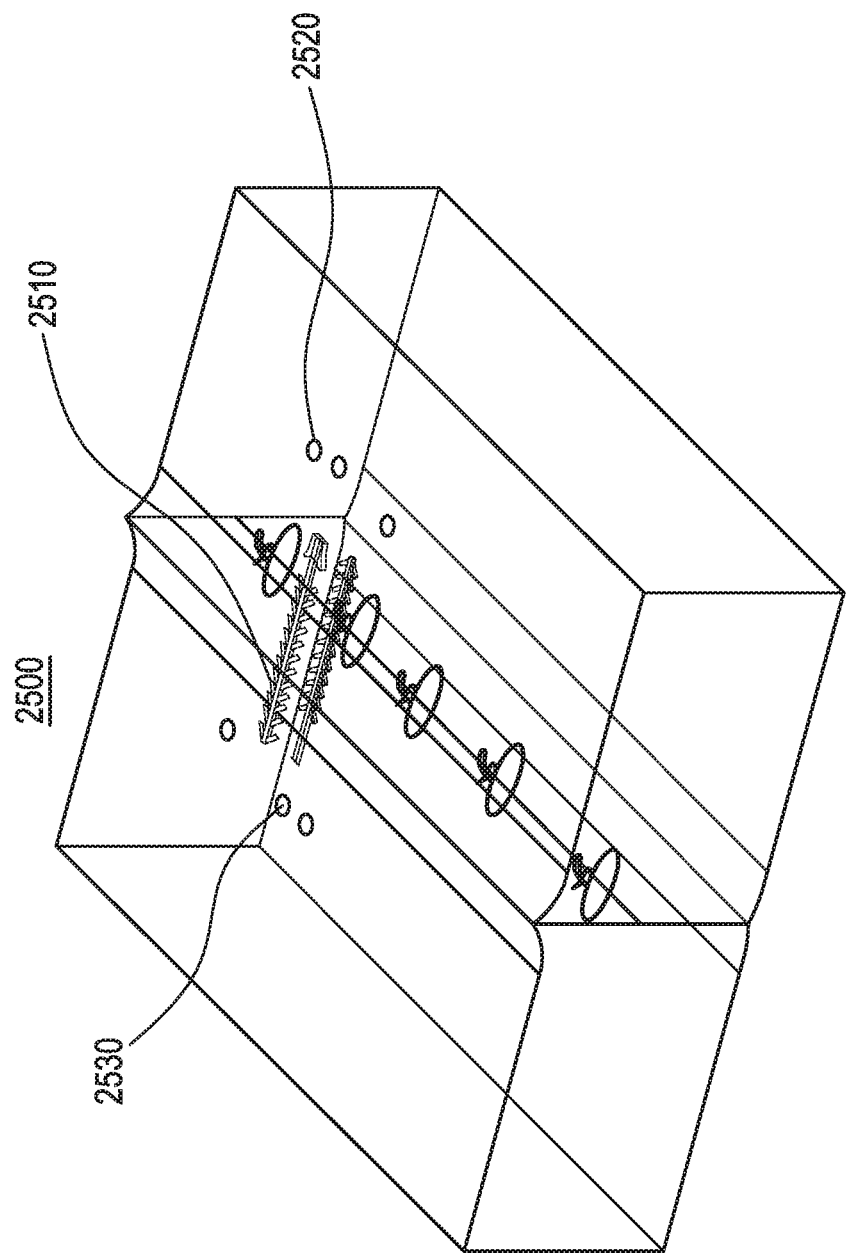
FIG. 25 is a schematic showing a section of dermal tissue and associated layers to illustrate the typical placement of the fastener post deployment.

Referring to FIG. 25, a section of dermal tissue and associated layers 2500 are illustrated to show the typical placement of the fastener post-deployment. The fasteners 2510 shown are optional embodiments or versions with a barbed segment and an anchoring portion. The location of the anchor is within the intra-cutaneous region of the patient's tissues. The sutures in the fascial tissue are included to allow the viewer to see that the fasteners 2510 as well as the sutures are in the deeper tissues and are not located on the surface of the tissue as the illustration may otherwise appear. Additionally, the outer puncture locations 2520 from the four tissue hooks are located in the dermal layer as well as the two inboard puncture sites 2530 from the styluses are shown for illustration purposes. In actuality, the puncture sites will close upon removal of the hooks and stylus units as is ordinary for punctures produced by injection needles and will heal without trace.

The instruments of the present invention can be made from a variety of conventional biocompatible materials using conventional manufacturing processes and techniques. The conventional biocompatible materials include but are not limited to stainless steel, aluminum, Nitinol, metal alloys, polymeric materials such as polycarbonate, polypropylene, polyethylene, ceramics, and the like and combinations thereof. The devices of the present invention may be made by various conventional manufacturing processes and techniques including but not limited to machining, stamping, cutting, molding, extruding, casting, etc., and the like.

The fasteners useful in the practice of the present invention can be made from a variety of conventional biocompatible materials using conventional manufacturing processes and techniques. The biocompatible materials include but are not limited to absorbable polymeric materials and nonabsorbable polymeric materials and combinations thereof. The absorbable materials may include absorbable polyester polymeric materials such as lactones, lactides, glycolides, ε-caprolactones, trimethylene carbonate, copolymers and combinations thereof and the like. The nonabsorbable materials may include polyolefins such as polyethylene and polypropylene, metals including stainless steels, metal alloys, and Nitinol, and the like. The conventional manufacturing techniques include but are not limited to extruding, stamping, cutting, machining, molding, casting, etc., and the like.

While the specific embodiments disclosed utilize fasteners that are placed through a compressive insertion method, other embodiments that utilize fasteners that are pulled into the tissue are also anticipated. In the alternate embodiments, the stylus units are actually driven into the tissue and the tips pass back out of the tissue and into the fastener feed plates. The distal tips of the stylus units may be produced with hook or other type engagement features that engage with mating reciprocal features on the fasteners which then enable the fastener to be pulled into the tissue under tension.

Although this invention has been shown and described with respect to detailed embodiments thereof, it will be understood by those skilled in the art that various changes in form and detail thereof may be made without departing from the spirit and scope of the claimed invention.

We claim:

1. A tissue fixation device, the device comprising: a handle member extending along a midline between a proximal end and a distal end, and having a top, a bottom, and a handle face at the distal end; first and second axle shafts each defining a respective longitudinal axis, rotatably connected to the distal end of the handle member, wherein the first and second axle shafts are located on opposite sides of the handle member midline and configured such that their respective longitudinal axis extend in a distal direction from the handle face; a tissue engagement trigger member having a proximal end and a distal end, the tissue engagement trigger member pivotally mounted to the handle member; a firing trigger pivotally mounted to the handle member; a tissue engagement end effector mounted to the distal end of the handle member and operably coupled to the tissue engagement trigger member through the first and second axle shafts for engaging and drawing tissue together and toward said tissue fixation device to thereby evert said tissue; said tissue engagement end effector comprising first and second curved tissue hooks each having a first end attached to the first and second axle shafts, respectively, and a second free end, wherein said second free ends are configured to rotate toward one another to thereby engage and evert said tissue when the first and second axle shafts are rotated about their respective longitudinal axis by actuation of the tissue engagement trigger member, and, an implant placement end effector mounted to the distal end of the handle member and operably coupled with the firing trigger for delivering at least one tissue fastener into tissue at a location distal of said first and second curved tissue hooks, wherein the implant placement end effector comprises a pair of opposed stylus members configured to pierce said tissue, pivotally mounted to the distal end of the handle member and positioned in offset opposing positions.

2. The device of claim 1, wherein the tissue engagement trigger member is operably connected to the tissue engagement end effector by a mechanism comprising pins and at least one lever member.

3. The device of claim 1, wherein the firing trigger is operably connected to the implant placement end effector by a mechanism comprising a plurality of pins and lever members.

4. The device of claim 1, wherein the tissue engagement trigger member is operably connected to the tissue engagement end effector by a mechanism comprising a plurality of meshing gears.

5. The device of claim 1, additionally comprising a pair of driver cam guides mounted on each side of the distal end of the handle member for engaging cam members mounted to the stylus members.

6. The device of claim 1, additionally comprising a feeder plate mounted to the bottom of the handle member at the distal end for receiving said at least one tissue fastener such that each stylus member can engage said at least one tissue fastener.

7. The device of claim 1, wherein the tissue engagement end effector is operably coupled to the tissue engagement trigger member by a mechanism comprising a plurality of pivotally connected members.

8. The device of claim 7 wherein the pivotally connected members comprise members selected from the group consisting of rods and bars.

9. The device of claim 1, wherein the implant placement end effector is operably coupled to the firing trigger by a mechanism comprising a plurality of meshing gears.

* * * * *